(12) United States Patent
Weise et al.

(10) Patent No.: US 9,238,843 B2
(45) Date of Patent: Jan. 19, 2016

(54) COMPOSITIONS AND METHODS FOR IDENTIFYING AND DIFFERENTIATING VIRAL COMPONENTS OF MULTIVALENT SHIPPING FEVER VACCINES

(75) Inventors: Dale Wade Weise, San Angelo, TX (US); James Robert Harris, Miles, TX (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/995,707

(22) PCT Filed: Dec. 21, 2011

(86) PCT No.: PCT/US2011/066392
§ 371 (c)(1),
(2), (4) Date: Jun. 19, 2013

(87) PCT Pub. No.: WO2012/092054
PCT Pub. Date: Jul. 5, 2012

(65) Prior Publication Data
US 2013/0266934 A1 Oct. 10, 2013

Related U.S. Application Data

(60) Provisional application No. 61/427,404, filed on Dec. 27, 2010.

(51) Int. Cl.
*C12Q 1/70* (2006.01)
(52) U.S. Cl.
CPC . *C12Q 1/70* (2013.01); *C12Q 1/701* (2013.01)
(58) Field of Classification Search
USPC ........................................................ 435/6.12
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,415,732 A | 11/1983 | Caruthers et al. | |
| 4,458,066 A | 7/1984 | Caruthers et al. | |
| 4,683,195 A | 7/1987 | Mullis et al. | |
| 4,683,202 A | 7/1987 | Mullis | |
| 4,725,677 A | 2/1988 | Koster et al. | |
| 4,800,159 A | 1/1989 | Mullis et al. | |
| 4,973,679 A | 11/1990 | Caruthers et al. | |
| 4,980,460 A | 12/1990 | Molko et al. | |
| 5,279,721 A | 1/1994 | Schmid | |
| 5,614,388 A | 3/1997 | Picone et al. | |
| 5,733,555 A | 3/1998 | Chu | |
| 6,610,305 B1 * | 8/2003 | Elbers et al. ............... | 424/218.1 |
| 6,921,535 B2 * | 7/2005 | Buchholz et al. ........... | 424/211.1 |
| 2004/0037850 A1 * | 2/2004 | Buchholz et al. ........... | 424/204.1 |
| 2011/0070586 A1 * | 3/2011 | Slezak et al. ...................... | 435/6 |

FOREIGN PATENT DOCUMENTS

| | | | | |
|---|---|---|---|---|
| CN | 101696453 A | | 4/2010 | |
| FR | WO2004073737 | * | 9/2004 | ............. A61K 39/12 |
| WO | WO-01/39801 A2 | | 6/2001 | |
| WO | WO-2004/073737 A1 | | 9/2004 | |
| WO | WO-2005/089793 A1 | | 9/2005 | |
| WO | WO-2007/094854 A2 | | 8/2007 | |
| WO | WO-2007/117303 A2 | | 10/2007 | |

OTHER PUBLICATIONS

Lowe T, Sharefkin J, Yang SQ, Dieffenbach CW. A computer program for selection of oligonucleotide primers for polymerase chain reactions. Nucleic Acids Res.Apr. 11, 1990; 18(7):1757-61.*
Boxus M, Letellier C, Kerkhofs P. Real Time RT-PCR for the detection and quantitation of bovine respiratory syncytial virus. J Virol Methods. May 2005;125(2):125-30.*
Genbank Accession No. S40504.1 Nucleocapsid protein [bovine respiratory syncytial virus BRSV, strain 391-2 mRNA, 1197 nt] (GI:251865, submitted by Amann et al. 1992, retrieved on Oct. 1, 2013 from http://www.ncbi.nlm.nih.gov/nuccore/S40504).*
Abril C, Engels M, Liman A, Hilbe M, Albini S, Franchini M, Suter M, Ackermann M. Both viral and host factors contribute to neurovirulence of bovine herpesviruses 1 and 5 in interferon receptor-deficient mice. J Virol. Apr. 2004; 78(7):3644-53.*
Hakhverdyan, M., Hagglund, S., Larsen, L.E., Belak, S., 2005. Evaluation of a single-tube fluorogenic RT-PCR assay for detection of bovine respiratory syncytial virus in clinical samples.J. Virol. Methods 123, 195-202.*
Kuypers J, Wright N, Ferrenberg J, Huang Ml, Cent A, Corey L, Morrow R. Comparison of real-time PCR assays with fluorescent-antibody assays for diagnosis of respiratory virus infections in children. J Clin Microbiol. Jul. 2006; 44(7):2382-8.*

(Continued)

*Primary Examiner* — Samuel Woolwine
*Assistant Examiner* — Olayinka Oyeyemi
(74) *Attorney, Agent, or Firm* — David L. Pflugh

(57) ABSTRACT

Disclosed are methods and compositions for identifying viral-specific polynucleotide sequences in a biological sample, and particularly in samples of veterinary origin. Also disclosed are oligonucleotide primer pairs, as well as labeled oligonucleotide detection probes useful in detecting the presence of one or more particular species, strains, types, or subtypes of one or more mammalian pathogens of viral origin, as well as systems, diagnostic kits and articles of manufacture comprising virus-specific primers and labeled detection probes, including those useful in identifying viral components of a multivalent vaccine, and quantitating the potency of particular attenuated, live viruses that comprise a livestock vaccine. In certain embodiments, real-time, quantitative PCR methods have been utilized to identify and distinguish between the three known genetic subtypes of bovine viral diarrhea viruses (BVDV-1a, BVDV-1b, and BVDV-2) in a multivalent bovid shipping fever vaccine.

10 Claims, No Drawings

(56) References Cited

OTHER PUBLICATIONS

Larsen Le, Tjørnehoj K, Viuff B, Jensen Ne, Uttenthal A. Diagnosis of enzootic pneumonia in Danish cattle: reverse transcription-polymerase chain reaction assay for detection of bovine respiratory syncytial virus in naturally and experimentally infected cattle. J Vet Diagn Invest. Sep. 1999; 11(5):416-22.*

Genbank Accession No. AF092942.1—Bovine respiratory syncytial virus strain ATue51908 1, complete genome (GI: 4028550, submitted by Buchholz et al. Dec. 17, 1998, retrieved on May 23, 2014 from http://www.ncbi.nlm.nih.gov/nuccore/AF092942.1).*

Genbank Accession No. KF834226.1—Bovine viral diarrhea virus 1 isolate R07_2007-01-02 5'UTR, (GI: 574609404, retrieved on May 23, 2014 from http://www.ncbi.nlm.nih.gov/nuccore/ KF834226).*

Genbank Accession No. FJ223614—Bovine viral diarrhea virus 1 isolate CSFV 5' UTR and polyprotein gene, partial cds (GI: 209418876, submitted by Gerilovych , Sep. 18, 2008, retrieved on Jun. 11, 2014 from http://www.ncbi.nlm.nih.gov/nuccore/FJ223614).*

Rodriguez Medina, M. et al. Development and evaluation of a polymerase chain reaction assay to detect Bovine herpesvirus 1. Spanish Journal of Agricultural Research, [S.I.], vol. 7, No. 1, p. 59-66, Mar. 2009. ISSN 2171-9292. Available at: <http://revistas.inia.es/index.php/sjar/article/view/398/395>. Retrieved on May 22, 2014.*

Peters et al. (2004a). Real-time RT-PCR: considerations for efficient and sensitive assay design. J Immunol Methods. Mar. 2004; 286(1-2):203-17.*

Peters AR, Thevasagayam SJ, Wiseman A, Salt JS. Duration of immunity of a quadrivalent vaccine against respiratory diseases caused by BHV-1, PI3V, BVDV, and BRSV in experimentally infected calves. Prev Vet Med. Dec. 15, 2004; 66(1-4):63-77.*

Willoughby K, Thomson K, Maley M, Gilray J, Scholes S, Howie F, Caldow G, Nettleton PF. Development of a real time reverse transcriptase polymerase chain reaction for the detection of bovine respiratory syncytial virus in clinical samples and its comparison with immunohistochemistry and immunofluorescence antibody testing. Vet Microbiol. Jan. 1, 2008.*

Lowe T, Sharefkin J, Yang SQ, Dieffenbach CW. A computer program for selection of oligonucleotide primers for polymerase chain reactions. Nucleic Acids Res. Apr. 11, 1990; 18(7):1757-61.*

Pennathur S, Haller AA, MacPhail M, Rizzi T, Kaderi S, Fernandes F, Bicha L, Schickli JH, Tang RS, Chen W, Nguyen N, Mathie S, Mehta H, Coelingh KL. Evaluation of attenuation, immunogenicity and efficacy of a bovine parainfluenza virus type 3 (PIV-3) vaccine and a recombinant chimeric bovine/human PIV-3 vaccine vector in rhesus monkeys. J Gen Viro.*

Letellier C, Kerkhofs P. Real-time PCR for simultaneous detection and genotyping of bovine viral diarrhea virus. J Virol Methods. Dec. 2003; 114(1):21-7.*

Liu L, Xia H, Belák S, Baule C. A TaqMan real-time RT-PCR assay for selective detection of atypical bovine pestiviruses in clinical samples and biological products. J Virol Methods. Dec. 2008;154(1-2):82-5. Epub Oct. 14, 2008.*

Zulauf Brian J. Multiplex real-time RT-PCR in the detection and differentiation of bovine respiratory disease pathogens. Ph.D. Diss Jun. 14, 2007.*

Tjørnehøj K, Uttenthal A, Viuff B, Larsen Le, Røntved C, Rønsholt L. An experimental infection model for reproduction of calf pneumonia with bovine respiratory syncytial virus (BRSV) based on one combined exposure of calves. Res Vet Sci. Feb. 2003; 74(1):55-65.*

West K, Petrie L, Konoby C, Haines DN, Cortese V, Ellis JA. The efficacy of modified-live bovine respiratory syncytial virus vaccines in experimentally infected calves. Vaccine. Dec. 10, 1999; 18(9-10):907-19.*

Ridpath JF. Immunology of BVDV vaccines. Biologicals. Jan. 2013; 41(1):14-9. Epub Aug. 9, 2012.*

Giangaspero M, Vacirca G, Harasawa R, Büttner M, Panuccio A, De Giuli Morghen C, Zanetti A, Belloli A, Verhulst A. Genotypes of pestivirus RNA detected in live virus vaccines for human use. J Vet Med Sci. Jul. 2001; 63(7): 723-33.*

Willoughby K, Valdazo-González B, Maley M, Gilray J, Nettleton PF. Development of a real time RT-PCR to detect and type ovine pestiviruses. J Virol Methods. Mar. 2006; 132(1-2):187-94. Epub Nov. 23, 2005.*

Xue et al. Immunogenicity of a modified-live virus vaccine against bovine viral diarrhea virus types 1 and 2, infectious bovine rhinotracheitis virus, bovine parainfluenza-3 virus, and bovine respiratory syncytial virus when administered intranasally in young calves. Vaccine. May 14, 2010; 28(22):3784-92. Epub Apr. 8, 2010.*

Genbank Accession No. M31182, Bovine viral diarrhea virus 1-NADL, complete genome (GI: 323205, submitted by Collett et al. Nov. 2005, retrieved on Jan. 28, 2015 from http://www.ncbi.nlm.nih.gov/nuccore/M31182).*

De Moerlooze L, Lecomte C, Brown-Shimmer S, Schmetz D, Guiot C, Vandenbergh D, Allaer D, Rossius M, Chappuis G, Dina D, et al. Nucleotide sequence of the bovine viral diarrhoea virus Osloss strain: comparison with related viruses and identification of specific DNA probes in the 5' untranslated region. J Gen Virol. Jul. 1993; 74 (Pt 7):1433-8.*

Hornberg A, Fernández SR, Vogl C, Vilcek S, Matt M, Fink M, KÖfer J, Schöpf K. Genetic diversity of pestivirus isolates in cattle from Western Austria. Vet Microbiol. Mar. 30, 2009; 135(3-4):205-13. Epub Sep. 26, 2008.*

Genbank Accession No. AB042684.1—Bovine viral diarrhea virus 1 gene, 5'UTR, partial sequence, strain HKD 858NCP/95 (GI: 14324184, submitted by Nagai et al. May 2010, retrieved on Aug. 11, 2015 from http://www.ncbi.nlm.nih.gov/nuccore/AB042684).*

Nagai M, Ito T, Sugita S, Genno A, Takeuchi K, Ozawa T, Sakoda Y, Nishimori T, Takamura K, Akashi H. Genomic and serological diversity of bovine viral diarrhea virus in Japan. Arch Virol. 2001; 146(4):685-96.*

Sakoda Y, Ozawa S, Damrongwatanapokin S, Sato M, Ishikawa K, Fukusho A. Genetic heterogeneity of porcine and ruminant pestiviruses mainly isolated in Japan. Vet Microbiol. Feb. 23, 1999;65(1):75-86.*

Hu, et al., Development of a real-time RT-PCR assay for detection and quantitation of parainfluenza virus 3", Journal of Virological Methods, 2005, vol. 130, pp. 145-148.

Olafson, et al., An Apparently New Transmissible Disease of Cattle, Cornell Vet., 1946, 36, pp. 205-213.

Wren, et al., "New Thinking on BRSV: Research into BRSC and vaccines reveals new information about how the virus behaves and how it may interact with killed vaccines", Bovine Veternarian, Feb. 2001. pp. 16-19.

Xue, et al., "Vaccination with a modified-live bovine viral diarrhea virus (BVDV) type 1a vaccine completely protected calves against challenge with BVDV type 1b strains", Vaccine, 2011, vol. 29, pp. 70-76.

Yeş ilbağ, et al., "Seroprevalence of bovine respiratory viruses in North-Westen Turkey", Trop Anim Health Prod. 2008, vol. 40, pp. 55-60.

Robert W. Fulton, et al., "Bovine viral diarrhea virus (BVDV) 1b: predominant BVDV subtype in calves with respiratory disease", The Canadian Journal of Veterinary Research, Canadian Veterinary Medical Association, Ottawa, CA, Vo. 66, No. 3, Jul. 1, 2002, pp. 181-190.

Nathalie Vanderheijden, et al., "Expression of the bovine viral diarrhoea virus Osloss p80 protein: its use as ELISA antigen for cattle serum antibody detection", Journal of General Virology, vol. 74, No. 7, 1993, pp. 1427-1431.

N. Mishra et al. "Genetic Analysis of Indian Bovine Viral Diarrhea Virus 1 Isolates in $N^{pro}$ and Entire Gene Region Coding Structural Proteins", Acta Virologica, vol. 50, No. 1, 2006, pp. 39-44.

John C. Baker, et al., "Study on the etiologic role of bovine respiratory syncytial virus in pneumonia of dairy calves", JAVMA, vol. 189, No. 1, Jul. 1, 1986, pp. 66-70.

D. M. L. Barber, et al., "Disease in a dairy herd associated with the introduction and spread of bovine virus diarrhoea virus", The Veterinay Record, vol. 117, 1985, pp. 459-464.

(56) References Cited

OTHER PUBLICATIONS

A. Terenzi, et al., "Efficacy of Fludarabine as an Immunosuppressor for Bone Marrow Transplantation Conditioning: Preliminary Results", Transplantation Proceedings, vol. 28, No. 6, Dec. 1996, p. 3101.
Wenzhi Xue, et al., "Vaccination with a modified-live bovine viral diarrhea virus (BVDV) type 1a vaccine completely protected calves against challenge with BVDV type 1b strains", Vaccine, vol. 29, 2011, pp. 70-76.
Rosner, S.F., "Infectious Bovine Rhinotracheitis: Clinical Review, Immunity, and Control," J.A.V.M.A., vol. 153, No. 12, Dec. 1968, pp. 1631-1638.
Sambrook & Russell, *Molecular cloning: a laboratory manual*, 3rd Edition, Cold Spring Harbor Laboratory, Cold Spring Harbor, NY, USA, 2001.
Thiel, et al., "*The pestiviruses*," In Virology, Fieldds et al., (eds.) (Lippincott-Raven, Philadelphia, PA, USA), pp. 1059-1073, 1996.
Boxus, M., C. Letellier, and P. Kerkhofs, "Real time RT-PCR for the detection and quantitation of bovine respiratory syncytial virus," J. Virological Methods 125: 125-130, 2005.
Bryson, D.G., M.S. McNulty, R.T. Evans, and G. Allan, "Studies of the effect of recombinant human-alpha 1 interferon on experimental parainfluenza type 3 virus infections of the respiratory tract of calves," Veterinary Record 125(25): 615-618, 1989.
Fulton, R.W., "Bovine respiratory disease research (1983-2009)," Animal Health Research Reviews 10: 131-139, 2009.
Gribskov, M., A.D. McLachlan, and D. Eisenberg, "Profile analysis: detection of distantly related proteins," Proc. Natl. Acad. Sci. U.S.A. 84(13): 4355-4358, 1987.
Needleman, S.B., and C.D. Wunsch, "A general method applicable to the search for similarities in the amino acid sequence of two proteins," Journal of Molecular Biology 48(3): 443-453, 1970.
Pearson, W.R., and D.J. Lipman, "Improved tools for biological sequence comparison," Proc. Natl. Acad. Sci. U.S.A. 85(8): 2444-2448, 1988.
Sambrook and Russell, Molecular cloning: a laboratory manual, 3rd Edition, Cold Spring Harbor Laboratory, Cold Spring Harbor, N.Y., USA, 2001.
York, C.J., A.J.F. Schwarz, and L.A. Estella, "Isolation and Identification of Infectious Bovine Rhinotracheitis Virus in Tissue Culture," Proceedings of the Society for Experimental Biology and Medicine 94(4): 740-744, 1957.
U.S. Appl. No. 13/995,688, Eli Lily and Company.
Robert W. Fulton, et al., "Bovine viral diarrhea virus (BVDV) 1b: predomiant BVDV subtype in calves with respiratory disease", The Canadian Journal of Veterinary Research, Canadian Veterinary Medical Association, Ottawa, CA, Vo. 66, No. 3, Jul. 1, 2001, pp. 181-190.
Nathalie Vanderheijden, et al., "Expression of the bovine viral diarrhea virus Osloss p80 protein: its use as ELISA antigen for cattle serum antibody detection", Joruanl of General Virology, vol. 74, No. 7, 1993, pp. 1427-1431.
N. Mishra et al., "Genetic Analysis of Indian Bovine Viral Diarrhea Virus 1 Isolates in $N^{Pro}$ and Entire Gene Region Coding Structural Proteins" Acta Virologica, vol. 50, No. 1, 2006, pp. 39-44.
F.K. Ramsey, et al., "Mucosal Disease of Cattle", Iowa State College, Ames, Iowa, Sep. 1953, pp. 629-633.
John C. Baker, et al., "Study on the etiologic role of bovine respiratory syncytial virus in pneumonia of dairy calves" JAVMA, vol. 189, No. 1, Jul. 1, 1986, pp. 66-70.
Chritina E. Ross, et al., "Herd problem of abortions and malformed calves attributed to bovine viral diarrhea", JAVMA, vol. 188, No. 6, Mar. 15, 1986, pp. 618-619.
D. M. L. Barber, et al., "Disease in a dairy herd associated with the introduction and spread of bovine virus diarrhea virus", . The Veterinary Record, vol. 117, 1985, pp. 459-464.
Marc S. Collett, et al., "Proteins encoded by Bovine Viral Diarrhea Virus: The Genomic Organization of a Pestivirus", Virology, vol. 165, 1988, pp. 200-208.
Wenzhi Xue, et al., "Vaccination with a modified-live bovine viral diarrhea virus (BVDV) type 1a vaccine completely protected calves against challenge with BVDV type 1b strains", Vaccine, vol. 29, 2010, pp. 70-76.
W.A. Malmquist, "Bovine viral Diarrhea-Mucosal Disease: Etiology, Pathogenesis, and Applied Immunity", J.A.V.M.A., vol. 152, No. 6, Mar. 15, 1968, pp. 763-768.
James H. Gillespie, et al., "A Cytopathogenic Strain of Virus Diarrhea Virus", New York State Veterinary College, Ithaca, New York, received Sep. 30, 1959, pp. 73-79.
Sudhir Agrawal, et al., "Site Specific functionalization of Oligonucleotides for attaching two different reporter groups", Nucleic Acids Research, vol. 18, No. 16, 1990, pp. 5419-5423.
John C. Baker, "The Clinical Manifestations of Bovine Viral Diarrhea Infection", Bovine Viral Diarrhea Virus, vol. 11, No. 3, Nov. 1995, pp. 425-445.
Serge L. Beaucage, et al., "Advances in the Synthesis of Oligonucleotides by the Phosphoramidite Approach", Tetrahedron, vol. 48, No. 12, 1992, pp. 2223-2311.
Paul Becher, et al., "Further Characterization of Border Disease Virus Isolates: Evidence for the Presence of More Than Three Species within the Genus Pestivirus", Virology, vol. 209, 1995, pp. 200-206.
K. Elbers, et al., "Processing on the pestivirus E2-NS2 region: identification of proteins p7 and E2p7.", Journal of Virology. vol. 70, No. 6, Jun. 1996, pp. 4131-4135.
Eduardo F. Flores, et al., "Phylogenetic analysis of Brazilian bovine viral diarrhea virus type 2(BVDV-2) isolates: evidence for a subgenotype within BVDV-2", Virus Research, 87, 2002, pp. 51-60.
Robert W. Fulton, et al., "Evaluation of diagnostic tests used for detection of bovine viral diarrhea virus and prevalence of subtypes 1a, 1b, and 2a in persistently infected cattle entering a feedlot", JAVMA, vol. 228, No. 4, Feb. 15, 2006, pp. 578-584.
Charles Pellerin, et al., "Identification of a New Group of Bovine Viral Diarrhea Virus Strains Associated with Severe Outbreaks and High Mortalities", Virology, 203, 1994, pp. 260-268.
J.F. Ridpath, et al., "Segregation of Bovine Viral Diarrhea Virus Into Genotypes", Virology, 205, 1994. pp. 66-74.
Maryann Wiskerchen, et al., "Pestivirus Gene Expression: Protein p80 of Bovine Viral Diarrhea Virus is a Proteinase Involved in Polyprotein Processing", Virology, 184, 1991, pp. 341-350.
Jeremy Schefers, et al., "Serological evaluation of precolostral serum samples to detect *Bovine viral diarrhea virus* infections in large commercial dairy herds", Journal of Veterinary Diagnosis Investigation, 20, 2008, pp. 625-628.
J.E. Tanner, et al., "Design and analysis of veterinary vaccine efficacy trials", Veterinary Microbiology, 37, 1993, pp. 221-230.
M.A. Hofmann, et al., "Rapid characterization of new pestivirus strains by direct sequencing of PCR-amplified cDNA from the 5' noncoding region", Arch Virol, 139, 1994, pp. 217-229.
Pamela M. Holland, et al., "Detection of specific polymerase chain reaction product by utilizing the 5'→ 3' exonuclease activity of *Thermus aquaticus* DNA polymerase", Proc. Natl. Acad. Sci., vol. 88, Aug. 1991, pp. 7276-7280.
Hiroaki Ozaki, et al., "The estimation of distances between specific backbone-labeled sites in DNA using Fluorescence resonance energy transfer", Nucleic Acids Research, vol. 20, No. 19, 1992, pp. 5205-5214.
D. J. Paton, "Pestivirus Diversity", J. Comp. Path., vol. 112, 1995, pp. 215-236.
Todd Ranheim, et al., "Development and Application of a quantitative RT-PCR potency assay for a pentavalent rotavirus vaccine (RotaTeq®)", Journal of Virological Methods, 131, 2006, pp. 193-201.
Julia F. Ridpath, et al., "Differentiation of types 1a, 1b and 2 bovine viral diarrhea virus (BVDV) by PCR", Molecular and Cellular Probes, 12, 1998, pp. 101-106.
J.A.C. Schalk, et. al., "Potency estimation of measles, mumps and rubella trivalent vaccines with quantitative PCR infectivity assay", Biologicals, 33, 2005, pp. 71-79.
Johanna A.C. Schalk, et al., "Estimation of the number of infectious measels viruses in live virus vaccines using quantitative real-time PCR", Journal of Virological Methods, 117, 2004, pp. 179-187.

(56) References Cited

OTHER PUBLICATIONS

Norbert Tautz., et al., "Serine Protease of Pestiviruses: Determination of Cleavage Sites", Journal of Virology, vol. 71, Jul. 1997, pp. 5415-5422.

Š. Vilček, et al., "Bovine viral diarrhea virus genotype 1 can be separated into at least eleven genetic groups", Archives of Virology, 146, 2001, pp. 99-115.

Fubao Wang, et al., "Using QPCR to assign infectious potencies to adenovirus based vaccines and vectors for gene therapy: toward a universal method for the facile quantitation of virus and vector potency", Vaccine, 23, 2005, pp. 4500-4508.

J Xu, et al., "Bovine Viral Diarrhea Virus NS3 Serine Proteinase: Polyprotein Cleavage Sites, Cofactor Requirements, and Molecualr Model of an Enzyme Essential for Pestivirus Replication", Journal of Virology, vol. 71, Jul. 1997, pp. 5312-5322.

R. Ian Freshney, "Culture of Animal Cells, A Manual of Basic Technique, Second Edition", Department of Medical Oncology, Cancer Research Campaign Laboratories, University of Glasgow.

David J. Finney, "Statistical Method in Biological Assay, Third Edition", 1978.

M.S. McNulty, et al., "Applications of Immunofluorescence in Veterinary Viral Diagnosis", Recent Advances in Virus Diagnosis, A Seminar in the CEC Programme of Co-ordination of Research on Animal Pathology, held at the Veterinary Research Laboratories, Belfast, Northern Ireland. Sep. 22-23, 1983. pp. 15-26.

B. Liess, et al., "Observations and investigations concerning "Mucosal Disease"in Cattle—A Late Form of BVD-MD Virus Infection that can be Explained Immunologically, with the Criteria of a "Slow Virus Infection"?", Deutsche Tierarztliche Wochenschrift (German Veterinary Weekly) 81, Oct. 15, 1974, pp. 481-487, Includong English language translation.

J. Sambrook, et al., "Molecular Cloning, A Laboratory Manual, Second Edition", Cold Spring Harbor Laboratory Press, 1989.

International Search Report dated May 9, 2012 in PCT/US2011/066392 filed Dec. 21, 2011.

International Search Report dated Nov. 2, 2013 in PCT/US2011/066392 filed Dec. 21, 2011.

Li Tiansong, The Establishment and Primary Application of the Method of Detecting BVDV Fluorescence RT-PCR, Chinese Master's Theses Full-text Database, Issue 3, 2006.

\* cited by examiner

COMPOSITIONS AND METHODS FOR IDENTIFYING AND DIFFERENTIATING VIRAL COMPONENTS OF MULTIVALENT SHIPPING FEVER VACCINES

CROSS-REFERENCE TO RELATED APPLICATIONS

This application is the National Stage of International Application No. PCT/US2011/066392, filed Dec. 21, 2011, and claims benefit of U.S. Application No. 61/427,404, filed Dec. 27, 2010, both of which are herein incorporated by reference in their entirety.

SEQUENCE LISTING

The instant application contains a sequence listing which has been submitted in ASCII format via EFS-Web and is hereby incorporated by reference in its entirety. Said ASCII copy, created on Dec. 13,2011 is named X19558_ST25.txt and is 4,567 bytes in size.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

BACKGROUND OF THE INVENTION

1. Field of the Invention

The present invention relates generally to the field of molecular biology, and more specifically to veterinary clinical laboratory diagnostic methods. In particular, a system, method, compositions, and diagnostic kits are provided for identification, amplification, quantitation and/or detection of nucleic acid segments derived from specific viral species, types, and/or subtypes, including those species implicated as causal or contributory agents in bovine respiratory disease complex (BRDC). In particular, methods and compositions are disclosed for identifying and differentiating between the three known subgenotypes of Bovine Viral Diarrhea Virus (BVDV).

2. Description of Related Art

"SHIPPING FEVER"

"Shipping fever" is a term given to an acute, highly-contagious, septicemic syndrome in cattle and sheep that is characterized clinically by fever, acute inflammation of the airways, nasal discharge, anorexia, depression, fibrinous pneumonia, and necrosis of the infected tissues. Most frequently encountered in feedlots following shipping, shipping fever is the major cause of death among young cattle, and is responsible for an estimated annual loss to the industry of more than half a billion dollars. In 1991 alone, shipping fever was estimated cost the U.S. cattle industry almost $624 million, due primarily to the costs of treatment, production loss, and death.

The pathogenesis of shipping fever is generally considered to involve adverse external influences predisposing the animal to an initial viral respiratory infection, which, in turn, produces conditions favorable for the proliferation of one or more secondary bacterial infections.

Bovine Respiratory Disease (BRD) Complex (BRDC)

BRDC (often commonly referred to as "shipping fever.") is a multifactorial disease complex that frequently afflicts stocker/feeder calves in market channels and at destination pasture or feedlot. Characterized by concomitant sequential or simultaneous infection by both viral and bacterial pathogens, BRDC is a major cause of economic loss in the beef and dairy cattle industries.

The disease, which infects cattle of all ages (including nursing calves), is characterized by rapid breathing, coughing, depression, loss of appetite, ocular and nasal discharge, and elevated temperatures. In an acute outbreak, death may follow within 24 hours of onset of symptoms. Calves exhibiting depression will have drooping ears, an extended head, a bowed back and/or often isolate themselves from other cattle. As the health of the calves progressively deteriorates, they stop feeding, exhibit an increased respiratory rate, and develop a pronounced fever (typically in the 104°-108° F. range).

At least four viral pathogens have been implicated in BRDC. They include bovine herpes virus 1 (BHV-1) (the causal agent of infectious bovine rhinotracheitis [IBR]), bovine parainfluenza type 3 virus ($PI_3$), one or more genetic variants of bovine viral diarrhea virus (BVDV), and Bovine respiratory syncytial virus (BRSV).

Following viral infection, the affected animals then develop one or more subsequent bacterial infections (e.g., *Mannheimia* [formerly *Pasteurella*] *haemolytica*, *Pasteurella multocida*, *Histophilus somni* (formerly *Haemophilus somnus*), *Actinomyces pyogenes*, and various *Mycoplasma* spp.) which often manifest in acute pneumonia.

Bovine Viral Diarrhea Virus (BVDV)

BVDV is now recognized as an important etiologic agent in BRDC. Spread through a herd in a fecal-oral manner, the virus causes acute infections (including diarrhea, fever, and hemorrhagic syndrome), and is capable of crossing the placenta of pregnant cattle, which often results in the birth of persistently infected (PI) calves that are immunotolerant to the virus and persistently viremic for the rest of their lives. PI bovids currently represent the major reservoir of the virus; these animals are highly predisposed to infection with microorganisms causing pneumonia or enteric disease, and provide the necessary viral reservoirs for outbreaks of fatal mucosal disease (MD) in cattle (see e.g., Liess et al., 1974; Barber et al., 1985; Olafson et al., 1946; Ramsey et al., 1953; Malmquist, 1968; and Ross et al., 1986, each of which is specifically incorporated herein in its entirety by express reference thereto).

Bovine Viral Diarrhea viruses are a disparate group of viruses that can be classified both phenotypically (see, e.g., Baker, 1995) (cytopathic or noncytopathic) and genotypically (see, e.g., Ridpath et al., 1994; Vilcek et al., 2001; and Flores et al., 2002). Establishing protective immunity against BVDV in livestock has been problematic for a number of reasons. As in some other virally-mediated diseases, the levels of serum antibodies against BVDV do not necessarily correlate with protection against disease. Establishing protective immunity in nursing calves presents additional obstacles, since maternal antibodies to BVDV may deplete the injected immunogen and effectively neutralize the vaccine.

A study by Fulton et al. (2006) evaluated 21,743 calves entering U.S. feedlots and determined that 88 calves were persistently infected (PI) with BVDV. Of the 88 PI calves, 77.9% were infected with BVDV-1b; only 11.6% were infected with BVDV-1a, and only 10.5% were infected with BVDV-2a.

BRIEF SUMMARY OF THE INVENTION

The present invention overcomes these and other limitations inherent in the prior art by advantageously providing a system and method for detecting viral-specific nucleotide sequences in a population of polynucleotides in, or obtained from, a sample, and particularly samples of biological or veterinary origin. The present invention also overcomes deficiencies in the art in another embodiment by advantageously providing compositions and methods for specifically detecting and distinguishing between nucleic acids obtained from two or more genetically related polynucleotide populations, including, for example, nucleic acids obtained from two or more genetically related viral species, strains, types, or subtypes. The invention can provide, for the first time, specific oligonucleotide amplification primers and labeled oligonucleotide detection probes (as well as diagnostic assay kits comprising them), for discriminating between polynucleotides specific to the known genetic subtypes of BVDV (e.g., Type 1a, Type 1b, and Type 2), and for identifying and quantitating each viral component present in a polyvalent population of viral particles.

The invention also can advantageously provide amplification primer pairs and labeled oligonucleotide detection probes, as well as methods for using such compositions in varying embodiments for the preparation of highly-sensitive, viral-specific detection systems that may be exploited to more accurately determine potency of individual modified, live virus (MLV) in multivalent vaccine formulations, including for example, the hexavalent shipping fever vaccine set forth in Applicants' co-pending U.S. Provisional Patent Application 61/427,361 (filed Dec. 27, 2010, and specifically incorporated herein in its entirety by express reference thereto).

Also disclosed are articles of manufacture, including diagnostic kits that contain such viral-specific primers and probes. The rapid analyses and increased sensitivity provided using quantitative (and in particular, real-time quantitative) polymerase chain reaction (qPCR) assays that employ the compositions of the present invention (particularly when used in concert with one or more detectable labels, including, for example, fluorogenic and chromogenic detection methodologies, such as fluorescence resonance energy transfer (FRET)-based detection systems), illustrate just two of the many advantages the invention may offer to the veterinary clinical laboratory environment.

In a first embodiment, the invention provides a composition that includes at least a first viral-specific oligonucleotide amplification primer; at least a second viral-specific oligonucleotide amplification primer; and at least a first labeled, viral-specific detection probe suitable for conducting a PCR-based amplification/detection assay of a population of polynucleotides.

As noted herein, such viral-specific detection probes preferably include at least one detectable label, include, without limitation, one or more chromogenic, fluorogenic, spin-label or radioactive moieties, or any combination thereof.

In a related embodiment, the invention provides a composition for use in detecting one or more viral-specific nucleic acid sequences in an aqueous sample. Preferably the sample is a sample of biological origin (including, without limitation, cells, tissues, blood, plasma, serum, and any combinations thereof), or a diagnostic, laboratory, or pharmaceutical composition or formulation that is known to contain, or is suspected of containing, one or more viral-specific nucleic acids. Preferably, such composition is a mammalian vaccine formulation, or an immunogenic composition able of eliciting an immune response in one or more species of mammalian livestock.

Preferably, such compositions include one or more forward amplification primers, and one or more reverse amplification primers that specifically hybridize to, and facilitate the polymerase-dependent amplification of, a nucleic acid sequence that is specific for one or more bovine-pathogenic viral species, strains, types, and/or subtypes.

Further aspects of the invention include diagnostic and/or molecular assay kits as described in further detail herein that contain one or more of the aforementioned compositions, preferably suitable for performing a polymerase chain reaction to amplify a viral-specific nucleic acid sequence from a sample comprising a veterinary modified, live virus vaccine under appropriate conditions to produce a plurality of amplified nucleic acid segments via PCR that are detectable and/or quantifiable using one or more suitable labeled oligonucleotide detection probe(s), including, without limitation, those probe sequences described and exemplified herein.

The invention also provides use of one or more such compositions in the manufacture of an article for amplifying and/or detecting one or more viral-specific polynucleotides in a population of polynucleotides obtained from a biological sample. In illustrative embodiments, such use includes the amplification, detection, and/or quantitation of one or more BVDV particles, and preferably one or more such viral particles that are comprised with a MLV. In exemplary embodiments, use is demonstrated for such compositions in amplifying, detecting, and quantitating BVDV Type 1b, Type 1b, and Type 2-specific polynucleotide from a plurality of attenuated, live virus particles comprised within a multivalent, bovine shipping fever vaccine. By utilizing probe/primer combinations that are specific for various species, strains, types, or subtypes of viruses, the methods of the invention may be further employed in the characterization of vaccine potencies, and particularly in polyvalent, animal vaccines, such as those that are preventative for diseases such as BRDC and related shipping fevers having etiological agents of known viral origin.

In an overall and general sense, the methods of the present invention permit the rapid, accurate, and facile detection of viral-specific polynucleotides from within populations of polynucleotides, and in particular, from multivalent vaccine formulations effective in the prevention, treatment, management, and/or amelioration of one or more symptoms of multifactorial (and, particularly, diseases of multi-etiological origins) such as BRDC and related shipping fevers. Such method generally involves performing at least one cycling step, wherein the cycling step comprises at least a first amplifying step and at least a first hybridizing step, and wherein the at least a first amplifying step comprises contacting the sample with a probe/primer composition as disclosed herein, to produce a viral-specific amplification product if a viral-specific nucleic acid molecule is present in the sample, wherein the at least a first hybridizing step comprises contacting the sample with the composition; and contacting the amplification product so produced with at least a first labeled oligonucleotide detection probe under conditions effective to specifically detect the resulting hybridization product. In illustrative embodiments, the pair of viral-specific amplification primers comprises: a first oligonucleotide amplification primer of less than about 50 nucleotides in length, that comprises, consists essentially of, or alternatively, consists of, a nucleic acid sequence selected from one or more of SEQ ID NO:1, SEQ ID NO:19, SEQ ID NO:4, SEQ ID NO:7, SEQ ID NO:10, SEQ ID NO:13, and SEQ ID NO:16; and a second oligonucleotide amplification primer of less than about 50 nucleotides in length, that comprises, consists essentially of, or alternatively, consists of, a nucleic acid sequence selected from one or more of SEQ ID NO:2, SEQ ID NO:20, SEQ ID NO:5, SEQ ID NO:8, SEQ ID NO:11, SEQ ID NO:14, and SEQ ID NO:17.

In certain embodiments, the composition may further comprise at least a first labeled viral-specific detection probe. Such detection probes preferably are less than about 50 nucleotides in length, and comprise, consist essentially of, or alternatively, consist of, a nucleic acid sequence selected from one or more of SEQ ID NO:3, SEQ ID NO:21, SEQ ID NO:6, SEQ ID NO:9, SEQ ID NO:12, SEQ ID NO:15, and SEQ ID NO:18.

In preferred embodiments, the first cycling step preferably includes contacting the population of polynucleotides with a pair of viral-specific amplification primers to produce an amplification product when a viral-specific nucleic acid molecule is present in the population of polynucleotides, and further wherein the at least a first hybridizing step comprises contacting the population of polynucleotides with at least a first labeled viral-specific detection probe under conditions effective to detect the amplification product so produced. In certain embodiments, the detecting step may be performed in real time, and may further optionally include the additional step of determining the melting temperature between the viral-specific detection probe and the viral amplification product.

Methods and Compositions for Determination of Vaccine Potency

The present invention provides methods of identifying viral-specific polynucleotide sequences, and in particular, BVDV-specific polynucleotide sequences in a sample of MLV, such as those present in an animal vaccine. The invention also provides methods and compositions for specifically detecting viral-specific polynucleotide sequences in a sample, and particularly in a mammalian vaccine, or a veterinary or biological specimen obtained from a bovid, as well as from a vaccine candidate. The disclosed methods preferably utilize oligonucleotide primer pairs and labeled oligonucleotide probe compositions and kits, and particularly those comprising one or more of the sequences disclosed herein, for detecting PCR amplification products, labeling the resulting amplification products via a hybridized primer, and quantitating such amplification products using one or more of PCR, qPCR, RT-qPCR, and PCR/FRET-based assays, particularly in combination with subsequent melting curve (e.g., $C_T$) analysis.

In one embodiment, the invention provides a method for detecting the presence or absence of one or more viral-specific polynucleotides, or a nucleic acid segment that encodes all or a portion of a viral-derived protein, peptide or polypeptide. In certain aspects, one or more biological samples may be taken from an individual (for example, a vaccine formulation, or a biological sample obtained from a domestic livestock), and screened for the presence of such a sequence. In particular embodiments, the vaccine formulation or biological sample may be screened for the presence of one or more specific viral sequences, including, for example, a sequence specific to one or more of the MLV viral components of a multifactorial animal vaccine.

The process of PCR is well known to those of ordinary skill in the molecular biological arts (see, e.g., U.S. Pat. Nos. 4,683,195 and 4,683,202, each specifically incorporated herein in its entirety by express reference thereto). Template-dependent extension of primers in PCR is catalyzed by a polymerizing agent in the presence of adequate amounts of four deoxyribonucleotide triphosphates (dATP, dGTP, dCTP, and dTTP) in a reaction medium comprised of the appropriate salts, metal cations, and pH buffering system. Suitable polymerizing agents are enzymes known to catalyze template-dependent DNA synthesis. For example, if the template is RNA, a suitable polymerizing agent to convert the RNA into a complementary DNA (cDNA) sequence is reverse transcriptase (RT), such as avian myeloblastosis virus RT. As noted in U.S. Pat. No. 5,614,388 (specifically incorporated herein in its entirety by express reference thereto), if the target for amplification is DNA, suitable polymerases include, without limitation *E. coli* DNA polymerase I or its Klenow fragment, $T_4$ DNA polymerase, and Taq polymerase (a heat-stable DNA polymerase isolated from the microorganism, *Thermus aquaticus*). The latter enzyme, known as "Taq polymerase," is widely-used in the amplification and sequencing of nucleic acids, and the reaction conditions for using such polymerases are well known to those of ordinary skill in the art (see, e.g., Sambrook and Russell, 2001). In a preferred embodiment of the PCR process, the reaction is catalyzed by a thermostable DNA polymerase enzyme, such as Taq DNA polymerase, and carried out at an elevated temperature. The preferred temperature is one at which the enzyme is thermostable, and at which the nucleic acids are in an equilibrium of single and double strands, so that sufficient primer will anneal to template strands to allow a reasonable rate of polymerization. Strand separation is achieved by heating the reaction to a sufficiently high temperature for sufficient time to cause the denaturation of the duplex, but not to cause an irreversible denaturation of the polymerase.

In a particular application, the methods of the invention advantageously employ at least a first PCR-based amplification step, and preferably at least a first quantitative PCR-based amplification step, which generally involves performing at least one cycling step (which includes at least a first "amplifying" step and at least a first "hybridizing" step). This amplifying step includes contacting the sample with a pair of viral-specific oligonucleotide primers to produce an amplification product if a viral target polynucleotide was originally present in the sample. (Conversely, if no viral target polynucleotide was originally present in the sample, then no specific product amplification would be produced during the PCR process).

The hybridizing step typically includes contacting the sample that results from the amplifying step with one or more labeled oligonucleotide probes that specifically hybridize (i.e., bind to) the amplification product so produced. In cases of FRET analysis, the detection probe may comprise a first and a second member of a FRET-compatible detection pair of viral-specific oligonucleotide probes (including, for example, those FRET-compatible pairs that hybridize to the amplification product within no more than about four or five nucleotides of each other. In the case of FRET analysis, the first probe of the pair of detection probes is typically labeled with a donor fluorescent moiety and a second probe of the pair of detection probes is typically labeled with a corresponding acceptor fluorescent moiety. These detection probes, and the type of moieties that may be operably linked to them for use in the hybridizing step, have been described in more detail hereinabove.

The method also further comprises at least the step of detecting the presence or absence of the amplification product:probe hybrid through the use of a suitable label (and typically one operably linked to the probe), wherein the presence of a signal from the labeled probe is usually indicative of the presence of the target polynucleotide in the sample. Conversely, in the absence of a produced amplification product, substantially no detectable signal is obtained following the probe hybridization step, thereby indicative of the absence of the target polynucleotide in the population of nucleic acid sequences originally present in the analyzed sample.

In certain embodiments, the steps of amplification and detection may be performed in real time, and optionally the method may further include an additional quantitation or analytical step (including, for example, determining the melting temperature between the detection probe(s) and the corresponding amplification product to quantitate or further characterize the viral-derived target sequence (if present) in the analyzed sample.

The process of determining the melting temperature between a probe and its corresponding target generally involves the following: A PCR amplification product and the corresponding detection probe(s) are cooled to around 40° C. to facilitate the probe(s)' annealing to the complementary sequence(s) of the targeted PCR amplification product(s). Once the labeled probe(s) have been contacted with the reaction mixture under conditions effective to anneal the probe(s) to the targeted PCR product (if present), the detectable label (e.g., fluorophores, etc.) is then detected (and subsequently quantified) using conventional techniques known to those of ordinary skill in the molecular biology arts.

The detection of nucleic acids is well known to those of ordinary skill in the art, and may be achieved through the application of numerous approaches. These methods are generally based upon the detection of a label or marker, such as any radioactive, fluorescent, biological or enzymatic tags or labels known in the art (see, e.g., U.S. Pat. Nos. 3,817,837; 3,850,752; 3,939,350; 3,996,345; 4,277,437; 4,275,149 and 4,366,241, each of which is specifically incorporated herein in its entirety by express reference thereto. Further examples of detectable labels that may utilized in the practice of the invention include paramagnetic ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Fluorescent moieties including, without limitation, rhodamine, fluorescein and renographin may also be used, with enzymes that generate a colored product upon contact with a chromogenic substrate being particularly preferred. Secondary binding ligands (including, without limitation, a second antibody and/or a biotin/avidin ligand binding arrangement), may also be used, as is known to those of ordinary skill in the molecular biological arts.

As described above, any label can be used as a label of an oligonucleotide probe as long as it fulfills the above-mentioned requirements and it interacts with a nucleic acid-specific label. Examples include, but are not limited to, LightCycler® RED 640, LightCycler® RED 705, TAMRA and Alexa 633. The label may be attached to an oligonucleotide at any position as long as the attachment does not influence the hybridization of the oligonucleotide. In particular applications, the label is usually operably linked to (i.e., bound, attached, linked, etc.) at either the 5' or the 21 end of the oligonucleotide probe molecule.

In addition to the oligonucleotides specifically set forth herein, additional nucleic acids may be designed and synthesized (for example, using a computer program such as OLIGO [Molecular Biology Insights Inc., Cascade, Colo., USA]) either as amplification primers or detection probes for use in the viral potency assays described herein. Typically, oligonucleotide primers and probes are from about 7 or 8 to about 60 or 80 or so nucleotides in length (e.g., 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, etc. nucleotides in length). "Viral-specific primer(s)" as used herein refer to oligonucleotide primer(s) that specifically anneal to nucleic acid sequence present within the genome of a particular selected virus, and facilitate initiation of polymerase synthesis of amplification products therefrom under appropriate conditions. Likewise, "viral-specific probe(s)" refer to oligonucleotide probe(s) that specifically anneal to nucleic acid sequences that are amplified by a suitable polymerase using the hybridized primer pairs under appropriate conditions, and are serially, concomitantly, sequentially, and/or subsequently detectable (and, preferably, quantifiable) using conventional oligonucleotide detection assays and such like.

Oligonucleotide Compositions

In one embodiment, the present invention provides oligonucleotide probes and primer sequences specific for viral-specific polynucleotides and amplification products produced therefrom, that are useful in hybridization to, and amplification of, corresponding homologous viral polynucleotide sequences, and in particular to sequences of modified, live viral particles present in an animal vaccine. In illustrative embodiments, exemplary oligonucleotide primer sequences are disclosed that are useful in the detection and amplification of particular genetic strains, types, and subtypes of BVDV-specific nucleic acid sequences.

The oligonucleotide primers and probes of the present invention are designed for the selective amplification and detection of viral-specific nucleic acid segments, and BVDV-specific polynucleotides (and amplification products derived therefrom) in particular. The disclosed primer sequences are suitable for use in hybridization methods, and in DNA amplification methods such as PCRT™-based amplification methods (including, for example, real-time-pPCR, RT-PCR, at RT-PCR/FRET-based genetic analyses). Likewise, the disclosed oligonucleotide detection probes are suitable for labeling with an appropriate label means for detection and quantitation of the products resulting from the amplification of nucleic acids using one or more pairs of the viral-specific amplification primers disclosed herein.

When labeled with appropriate markers, the oligonucleotide detection probes are particularly suited for fluorescence-based detection, including, for example, PCR, real-time PCR, quantitative PCR (qPCR), FRET-based analyses, and such like. For example, FRET-labeled detection methodologies are particularly useful in fluorimetric detection based on microvolume fluorimetry. Use of one or more of the disclosed amplification and detection oligonucleotides pairs is particularly contemplated in the combined RT-PCR™/microvolume fluorimetry FRET-based methodologies (RT-PCR™/FRET), and particularly in analyses facilitated by the "LightCycler®" instrumentation as developed by Idaho Technology, Inc., and now manufactured and marketed by Roche Molecular Systems.

For most embodiments, the inventor contemplates that the length of the selected probe and primer compositions of the invention will preferably be less than about 50 to 60 or so nucleotides in length, and more preferably, will be less than about 40 to 45 or so nucleotides in length, while other probes and primers of the invention may be on the order of about 30 to 35 or so nucleotides in length. In some embodiments, the length of the selected oligonucleotide primer sequences (e.g., "forward" and "reverse" primers) and/or the length of the selected detection probe sequences (e.g., "anchor" and "sensor" probes), will likely be on the order of about 20 to 30 or so nucleotides in length, although in some cases, the sizes of particular probes and primer sequences may be larger than that, and on the order of about 60 to 70 nucleotides in length. Alternatively, in some embodiments, it may be desirable to employ shorter probe and/or primer sequences, and as such, the oligonucleotides selected for practice of the invention may be on the order of about 15 to 20 or so nucleotides in length or even slightly shorter in some embodiments.

In the context of the present application, it is understood that all intermediate oligonucleotide lengths within the various ranges stated herein are contemplated to expressly fall within the scope of the present invention. To that end, oligonucleotides that are "less than about XX nucleotides in length" include all integers included within the range. For example, oligonucleotides that are "less than about 60 nucleotides in length" include oligonucleotides that are 59, 58, 57, etc. to 4, 3, 2, or 1 nucleotides in length and each is expressly within the scope of the present disclosure.

Oligonucleotides of the invention may be synthesized by a number of conventional approaches that are known to those of ordinary skill in the art (see, e.g., Ozaki et al., 1992; Agrawal et al., 1990 or the like) using standard methodologies, including phosphoramidite chemistry (see, e.g., Beaucage and Iyer, 1992; and U.S. Pat. Nos. 4,980,460; 4,725,677; 4,415,732; 4,458,066; and 4,973,679; and the like). Alternative chemistries, e.g., resulting in non-natural backbone groups, such as phosphorothioate, phosphoramidate, and the like, may also be employed provided that the hybridization efficiencies of the resulting oligonucleotides are not adversely affected. Preferably, the oligonucleotides are in the range of about 10 to about 120 nucleotides in length; more preferably, in the range of about 15 to about 100 nucleotides in length, and more preferably still, in the range of about 20 to about 80 nucleotides in length, although the precise sequence and length of an oligonucleotide may depend inter alia on the nature of the target nucleic acid sequence to which it hybridizes, since the binding location and length may be varied to achieve appropriate annealing and melting properties for a particular embodiment. Guidance for making such design choices can be found in many of the above-cited references describing the "Taqman®-type" assays employed in the example below and also described in detail in Holland et al. (1991). Each of the foregoing references is specifically incorporated herein in its entirety by express reference thereto.

Viral-Specific Amplification Primers

In the practice of the invention, forward and reverse amplification primers for use in the amplification of viral-specific polynucleotide sequences, and BVDV-encoding polynucleotide sequences in specific, preferably will comprise, consist essentially of, or alternatively, consist of, at least about 6 to at least about 25 (including each integer therebetween) or more contiguous nucleic acids from any one of the "forward" oligonucleotide primer sequences disclosed in SEQ ID NO:1, SEQ ID NO:19, SEQ ID NO:4, SEQ ID NO:7, SEQ ID NO:10, SEQ ID NO:13, or SEQ ID NO:16 or the "reverse" oligonucleotide primer sequences disclosed in SEQ ID NO:2, SEQ ID NO:20, SEQ ID NO:5, SEQ ID NO:8, SEQ ID NO:11, SEQ ID NO:14, or SEQ ID NO:17; or from oligonucleotide sequences that are at least about 90% identical to any one of the "forward" oligonucleotide primer sequences disclosed in SEQ ID NO:1, SEQ ID NO:19, SEQ ID NO:4, SEQ ID NO:7, SEQ ID NO:10, SEQ ID NO:13, or SEQ ID NO:16 or the "reverse" oligonucleotide primer sequences disclosed in SEQ ID NO:2, SEQ ID NO:20, SEQ ID NO:5, SEQ ID NO:8, SEQ ID NO:11, SEQ ID NO:14, or SEQ ID NO:17; or even from oligonucleotide sequences that are at least about 95% identical to any one of the "forward" oligonucleotide primer sequences disclosed in SEQ ID NO:1, SEQ ID NO:19, SEQ ID NO:4, SEQ ID NO:7, SEQ ID NO:10, SEQ ID NO:13, or SEQ ID NO:16, or the "reverse" oligonucleotide primer sequences disclosed in SEQ ID NO:2, SEQ ID NO:20, SEQ ID NO:5, SEQ ID NO:8, SEQ ID NO:11, SEQ ID NO:14, or SEQ ID NO:17.

In other embodiments, the preferred oligonucleotide forward and reverse amplification primer sequences of the invention may comprise, consist essentially of, or alternatively, consist of, any one of the "forward" oligonucleotide primer sequences disclosed in SEQ ID NO:1, SEQ ID NO:19, SEQ ID NO:4, SEQ ID NO:7, SEQ ID NO:10, SEQ ID NO:13, or SEQ ID NO:16 or the "reverse" oligonucleotide primer sequences disclosed in SEQ ID NO:2, SEQ ID NO:20, SEQ ID NO:5, SEQ ID NO:8, SEQ ID NO:11, SEQ ID NO:14, or SEQ ID NO:17, while in other embodiments, it may be desirable to employ primer sequences that consist essentially of any one of the "forward" oligonucleotide primer sequences disclosed in SEQ ID NO:1, SEQ ID NO:19, SEQ ID NO:4, SEQ ID NO:7, SEQ ID NO:10, SEQ ID NO:13, or SEQ ID NO:16, or the "reverse" oligonucleotide primer sequences disclosed in SEQ ID NO:2, SEQ ID NO:20, SEQ ID NO:5, SEQ ID NO:8, SEQ ID NO:11, SEQ ID NO:14, or SEQ ID NO:17, and while in still other embodiments, it may be desirable to employ primer sequences that consist of any one of the "forward" oligonucleotide primer sequences disclosed in SEQ ID NO:1, SEQ ID NO:19, SEQ ID NO:4, SEQ ID NO:7, SEQ ID NO:10, SEQ ID NO:13, or SEQ ID NO:16, or the "reverse" oligonucleotide primer sequences disclosed in SEQ ID NO:2, SEQ ID NO:20, SEQ ID NO:5, SEQ ID NO:8, SEQ ID NO:11, SEQ ID NO:14, or SEQ ID NO:17.

In yet additional embodiments, the forward and reverse amplification primer compositions preferred for the practice of the methods of the present invention may comprise, consist essentially of, or alternatively, consist of, a nucleic acid sequence that represents a contiguous nucleic acid sequence of about 6 to about 25 (including each integer therebetween) or more nucleotides as disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

Likewise, the primer compositions preferred for the practice of the amplification methods of the present invention may comprise, consist essentially of, or alternatively, consist of, a nucleic acid sequence that is about 90% identical to a contiguous nucleic acid sequence of about 6 to about 25 (including each integer therebetween), or more nucleotides as disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

Additionally, the amplification primer compositions preferred for the practice of the amplification methods of the present invention may comprise, consist essentially of, or alternatively, consist of, a nucleic acid sequence that is at least about 95% identical to any one of the oligonucleotide sequences disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

In other embodiments, the primer compositions preferred for the practice of the invention may comprise, consist essentially of, or alternatively, consist of, a nucleic acid sequence that is at least about 6 to at least about 25 (again, including each integer therebetween) or more contiguous nucleic acids selected from any one of the oligonucleotide sequences disclosed in any one of SEQ ID NO:1, SEQ ID NO:19, SEQ ID NO:2, SEQ ID NO:20, SEQ ID NO:4, SEQ ID NO:S, SEQ ID NO:7, SEQ ID NO:8, SEQ ID NO:10, SEQ ID NO:11, SEQ ID NO:13, SEQ ID NO:14, SEQ ID NO:16, or SEQ ID NO:17; or may consist essentially of an oligonucleotide sequence that is at least about 90% identical to any one of the oligonucleotide sequences disclosed in any one of SEQ ID NO:1, SEQ ID NO:19, SEQ ID NO:2, SEQ ID NO:20, SEQ ID NO:4, SEQ ID NO:S, SEQ ID NO:7, SEQ ID NO:8, SEQ ID NO:10, SEQ ID NO:11, SEQ ID NO:13, SEQ ID NO:14, SEQ ID NO:16, or SEQ ID NO:17; or even may consist essentially of an oligonucleotide sequence that is at least about 95% identical to any one of the oligonucleotide sequences disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

In certain embodiments, illustrative amplification primers of the invention are at least about 50 nucleotides in length and comprise, consist essentially or, or consist of a nucleotide sequence that comprises a nucleotide sequence as disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

In other embodiments, illustrative amplification primers of the invention are at least about 40 nucleotides in length and comprise, consist essentially of, or consist of a nucleotide sequence that comprises a nucleotide sequence as disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

In additional embodiments, illustrative amplification primers of the invention are at least about 30 nucleotides in length and comprise, consist essentially or, or consist of a nucleotide sequence that comprises a nucleotide sequence as disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

In still additional aspects of the invention, illustrative amplification primers of the invention are at least about 25 nucleotides in length and comprise, consist essentially of, or consist of a nucleotide sequence that comprises a nucleotide sequence as disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17, while in other aspects, illustrative amplification primers of the invention are at least about 20 or so nucleotides in length and comprise, consist essentially of, or consist of a nucleotide sequence that comprises a nucleotide sequence as disclosed in any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

In particular illustrative examples, the oligonucleotide primer compositions of the invention are less than about 50 nucleotides in length and comprise the nucleotide sequence of any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17, while in other illustrative examples, the oligonucleotide primer compositions of the invention are less than about 40 nucleotides in length and comprise the nucleotide sequence of any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17, and in other examples still, the oligonucleotide primer compositions of the invention are less than about 30 nucleotides in length and comprise the nucleotide sequence of any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

In some aspects of the invention, it may be desirable to employ oligonucleotide primer compositions in the practice of the methods disclosed herein that are less than about 45 or so nucleotides in length and that consist essentially of the nucleotide sequence of any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17, or compositions that are less than about 35 or so nucleotides in length and that consist essentially of the nucleotide sequence of any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17, while in other examples still, it may be desirable to employ oligonucleotide primer compositions that are less than about 25 or so nucleotides in length and that consist essentially of the nucleotide sequence of any one of SEQ ID NO:1, SEQ ID NO:19, SEQ ID NO:2, SEQ ID NO:20, SEQ ID NO:4, SEQ ID NO:5, SEQ ID NO:7, SEQ ID NO:8, SEQ ID NO:10, SEQ ID NO:11, SEQ ID NO:13, SEQ ID NO:14, SEQ ID NO:16, or SEQ ID NO:17.

Viral-Specific Detection Probes

In the practice of the invention, oligonucleotide probes for use in the detection of viral-specific polynucleotide sequences (and BVDV-specific polynucleotide sequences in specific) using RT-qPCRT™ analysis as described herein, will preferably comprise at least about 6 to at least about 25 (including each integer therebetween) or more contiguous nucleic acids from any one of the oligonucleotide probe sequences disclosed in SEQ ID NO:3, SEQ ID NO:21, SEQ ID NO:6, SEQ ID NO:9, SEQ ID NO:12, SEQ ID NO:15, or SEQ ID NO:18; or from oligonucleotide sequences that are at least about 90% identical to any one of the oligonucleotide detection probe sequences disclosed in SEQ ID NO:3, SEQ ID NO:21, SEQ ID NO:6, SEQ ID NO:9, SEQ ID NO:12, SEQ ID NO:15, or SEQ ID NO:18; or even from oligonucleotide sequences that are at least about 95% identical to any one of the oligonucleotide probe sequences disclosed in SEQ ID NO:3, SEQ ID NO:21, SEQ ID NO:6, SEQ ID NO:9, SEQ ID NO:12, SEQ ID NO:15, or SEQ ID NO:18.

In other embodiments, the preferred oligonucleotide detection probes of the invention may comprise, consist essentially of, or alternatively, consist of, any one of the oligonucleotide probe sequences disclosed in SEQ ID NO:3, SEQ ID NO:21, SEQ ID NO:6, SEQ ID NO:9, SEQ ID NO:12, SEQ ID NO:15, or SEQ ID NO:18, while in other embodiments, it may be desirable to employ detection probe nucleic acid segments that consist essentially of any one of the oligonucleotides as disclosed in SEQ ID NO:3, SEQ ID NO:21, SEQ ID NO:6, SEQ ID NO:9, SEQ ID NO:12, SEQ ID NO:15, or SEQ ID NO:18, and while in still other embodiments, it may be desirable to employ probe sequences that consist of any one of the oligonucleotide sequences disclosed in SEQ ID NO:3, SEQ ID NO:21, SEQ ID NO:6, SEQ ID NO:9, SEQ ID NO:12, SEQ ID NO:15, or SEQ ID NO:18.

In yet additional embodiments, and specifically wherein FRET analysis is employed to detect the amplification products so produced, the detection probes of the present invention will preferably comprise a pair of probes, the first of which is an "anchor" probe, and the second of which is a "sensor" probe.

The probe compositions preferred for the practice of the methods of the present invention may comprise, consist essentially of, or alternatively, consist of, a pair of detection probes, the first and second members of which may consist of a nucleic acid sequence that represents a contiguous nucleic acid sequence of about 6 to about 25 (including each integer therebetween) or more nucleotides as disclosed in any one of SEQ ID NO:3, SEQ ID NO:21, SEQ ID NO:6, SEQ ID NO:9, SEQ ID NO:12, SEQ ID NO:15, or SEQ ID NO:18.

Likewise, probe compositions preferred for the practice of FRET-based detection methods may comprise, consist essentially of, or alternatively, consist of, a pair of detection probes, the first member of which may consist of a nucleic acid sequence that is about 80%, at least about 81% identical, at least about 82% identical, at least about 83%, at least about 84% or at least about 85% identical to a contiguous nucleic acid sequence of about 6 to about 25 (including each integer therebetween), or more nucleotides as disclosed in any one of SEQ ID NO:3, SEQ ID NO:21, SEQ ID NO:6, SEQ ID NO:9, SEQ ID NO:12, SEQ ID NO:15, or SEQ ID NO:18, while the second member of which pair of detection probes may preferably comprise, consist essentially of, or alternatively, consist of, a nucleic acid sequence that is about 90%, at least about 91% identical, at least about 92% identical, at least about 93%, at least about 94% or at least about 95% identical to a contiguous nucleic acid sequence of about 6 to about 25 (including each integer therebetween), or more nucleotides as disclosed in any one of SEQ ID NO:3, SEQ ID NO:21, SEQ ID NO:6, SEQ ID NO:9, SEQ ID NO:12, SEQ ID NO:15, or SEQ ID NO:18.

Additionally, when FRET-based analysis of the amplification products is desired, oligonucleotide probes preferred for the practice of the methods of the present invention may comprise, consist essentially of, or alternatively, consist of, a pair of FRET detection probes, the first and second members of which may comprise nucleic acid sequences that are at least about 95%, at least about 96% identical, at least about 97% identical, or at least about 98% or 99% identical to any one of the oligonucleotide sequences disclosed in any one of SEQ ID NO:3, SEQ ID NO:21, SEQ ID NO:6, SEQ ID NO:9, SEQ ID NO:12, SEQ ID NO:15, or SEQ ID NO:18. In other embodiments, the probe compositions preferred for the practice of the invention may comprise, consist essentially of, or alternatively, consist of, a pair of FRET anchor/sensor probes, the first and second members of which may consist essentially of a nucleic acid sequence that is at least about 6 to at least about 25 (including each integer there between) or more contiguous nucleic acids selected from any one of the oligonucleotide sequences disclosed in any one of SEQ ID NO:3, SEQ ID NO:21, SEQ ID NO:6, SEQ ID NO:9, SEQ ID NO:12, SEQ ID NO:15, or SEQ ID NO:18; or may consist essentially of an oligonucleotide sequence that is at least about 90% identical to any one of the oligonucleotide sequences disclosed in any one of SEQ ID NO:3, SEQ ID NO:21, SEQ ID NO:6, SEQ ID NO:9, SEQ ID NO:12, SEQ ID NO:15, or SEQ ID NO:18; or even may consist essentially of an oligonucleotide sequence that is at least about 95%, at least about 96% identical, at least about 97% identical, or at least about 98% or 99% identical to any one of the oligonucleotide sequences disclosed in any one of SEQ ID NO:3, SEQ ID NO:21, SEQ ID NO:6, SEQ ID NO:9, SEQ ID NO:12, SEQ ID NO:15, or SEQ ID NO:18.

In certain embodiments, illustrative viral amplification product-specific oligonucleotide detection probe compositions of the invention preferably are at least about 50 or so nucleotides in length, that either comprise, consist essentially of, or consist of, a nucleotide sequence selected from the group consisting of SEQ ID NO:3, SEQ ID NO:21, SEQ ID NO:6, SEQ ID NO:9, SEQ ID NO:12, SEQ ID NO:15, or SEQ ID NO:18.

In other embodiments, illustrative detection probe compositions of the invention preferably are oligonucleotides of at least about 40 or so nucleotides in length, that either comprise, consist essentially of, or consist of, a nucleotide sequence selected from the group consisting of SEQ ID NO:3, SEQ ID NO:21, SEQ ID NO:6, SEQ ID NO:9, SEQ ID NO:12, SEQ ID NO:15, or SEQ ID NO:18.

In other embodiments, detection probe compositions may be oligonucleotides of at least about 30 or so nucleotides in length, that either comprise, consist essentially of, or consist of, a nucleotide sequence selected from the group consisting of SEQ ID NO:3, SEQ ID NO:21, SEQ ID NO:6, SEQ ID NO:9, SEQ ID NO:12, SEQ ID NO:15, or SEQ ID NO:18, while in other embodiments still, suitable detection oligonucleotides may be at least about 20 or so nucleotides in length, that either comprise, consist essentially of, or consist of, a nucleotide sequence selected from the group consisting of SEQ ID NO:3, SEQ ID NO:21, SEQ ID NO:6, SEQ ID NO:9, SEQ ID NO:12, SEQ ID NO:15, or SEQ ID NO:18.

In particular illustrative examples, the oligonucleotide detection probe compositions of the invention are less than about 50 or so nucleotides in length and comprise the nucleotide sequence of any one of SEQ ID NO:3, SEQ ID NO:21, SEQ ID NO:6, SEQ ID NO:9, SEQ ID NO:12, SEQ ID NO:15, or SEQ ID NO:18, while in other illustrative examples, the oligonucleotide detection probe compositions are less than about 40 nucleotides in length and comprise the nucleotide sequence of any one of SEQ ID NO:3, SEQ ID NO:21, SEQ ID NO:6, SEQ ID NO:9, SEQ ID NO:12, SEQ ID NO:15, or SEQ ID NO:18.

In other applications, suitable oligonucleotide detection probes may be less than about 30 nucleotides in length and may comprise a nucleotide sequence selected from the group consisting of SEQ ID NO:3, SEQ ID NO:21, SEQ ID NO:6, SEQ ID NO:9, SEQ ID NO:12, SEQ ID NO:15, or SEQ ID NO:18.

In some aspects of the invention, it may be desirable to employ oligonucleotide probe compositions in the practice of the methods disclosed herein that are less than about 45 or so nucleotides in length and that consist essentially of the nucleotide sequence of any one of SEQ ID NO:3, SEQ ID NO:21, SEQ ID NO:6, SEQ ID NO:9, SEQ ID NO:12, SEQ ID NO:15, or SEQ ID NO:18, or alternatively, oligonucleotide probes that are less than about 35 or so nucleotides in length and that consist essentially of the nucleotide sequence of any one of SEQ ID NO:3, SEQ ID NO:21, SEQ ID NO:6, SEQ ID NO:9, SEQ ID NO:12, SEQ ID NO:15, or SEQ ID NO:18, while in other examples still, it may be desirable to employ oligonucleotide detection probe compositions that are less than about 25 or so nucleotides in length and that consist essentially of the nucleotide sequence of any one of SEQ ID NO:3, SEQ ID NO:21, SEQ ID NO:6, SEQ ID NO:9, SEQ ID NO:12, SEQ ID NO:15, or SEQ ID NO:18.

In illustrative embodiments, the invention provides viral-specific amplification primers and detection probes that comprise, consist essentially of, or consist of, nucleic acid sequences that are preferably at least about 80%, at least about 85%, at least about 90%, at least about 95%, at least about 96%, at least about 97%, at least about 98%, or at least about 99% or more identical to any one or more of the oligonucleotide sequences disclosed in SEQ ID NO:1 through SEQ ID NO:18.

In certain embodiments, the present invention provides sets of primers and probes designed based on their specific binding to one or more portions of a viral-specific amplification product. These probes and primers are particularly useful in a method for rapidly detecting and identifying viral-specific polynucleotide sequences in a biological sample. In particular embodiments, these methods involve real-time quantitation, including, without limitation, quantitative PCT (qPCR), reverse transcriptase-PCR(RT-PCR), and/or RT-PCR/Fluorescent Resonance Energy Transfer (FRET) (RT-PCR/FRET)-based amplification, detection, and/or quantitation methods.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Pestiviruses

Pestiviruses cause economically important diseases in animals worldwide. The genus *Pestivirus*, within the family Flaviviridae, comprises three species of single-stranded positive-sense RNA viruses: bovine viral diarrhea virus (BVDV), classical swine fever virus (CSFV), border disease virus (BDV). Recently, a fourth, distinct group of pestiviruses has been identified that is genetically related to BVDV, and is referred to in the literature as bovine viral diarrhea virus Type 2 (BVDV-2) (see e.g., Thiel et al., 1996; and Becher et al., 1995; each of which is specifically incorporated herein in its entirety by express reference thereto). Consequently, contemporary texts now refer to the original species of BVDV as "BVDV-1" to distinguish between the two species.

The type species of *Pestivirus* is BVDV Type 1 (BDVD-1), whose genome is approximately 12.5-kb in length and contains one large open reading frame (ORF) (Collett et al., 1988, specifically incorporated herein in its entirety by express reference thereto). The ORF codes for a large polyprotein of approximately 450 kDa that is processed co- and post-translationally by host or viral proteases. The N-terminal end of standard BVDV polyprotein results in a non-structural protein p20 (Npro), capsid protein p14 (C); envelope glycoproteins gp48 (E0), gp25 (E1), gp53 (E2); non-structural proteins p125 (NS23), p10 (NS4A), p32 (NS4B), p58 (NSSA) and p75 (NSSB) (see, e.g., Tautz et al., 1997; Xu et al., 1997; Elbers et al., 1996; and Wiskerchen et al., 1991, each of which is specifically incorporated herein in its entirety by express reference thereto). BVDV-1 exists in two biotypes, cytopathic (designated "cp") or non-cytopathic ("ncp"), which typically differ by the production of a single 80-kDa polypeptide (non-structural protein p80, NS3) in the cytopathic variant (see, e.g., Gillespie et al., 1960, specifically incorporated herein in its entirety by express reference thereto).

Based on phylogenetic analysis of a number of BVDV isolates, BVDV-1 has been shown to comprise at least 13 distinct subgenotypes (designated BVDV-1a to BVDV-11), while two subgenotypes (BVDV-2a and BVDV-2b) have been identified for BVDV-2 (see, e.g., Pellerin et al., 1994; Ridpath et al., 1994, and Xue et al., 2010; each of which is specifically incorporated herein in its entirety by express reference thereto).

In the past thirty years, nearly one hundred and fifty vaccines for BVDV, both modified live virus (MLV) and inactivated attenuated virus or virus particles, have been marketed to the cattle industry will varying degrees of success; outbreaks of BVDV are still reported on an annual basis despite the widespread availability and use of commercial vaccine formulations. Current approaches to disease management involve repeated yearly inoculation with vaccine for cattle, and additional steps are generally taken in an attempt to insure that no calves are born as PI carriers. Several different test methods have been developed for the detection of BVDV, and/or the detection of BVDV-infected animals, include reverse transcription-polymerase chain reaction (RT-PCR), enzyme-linked immunoassay (ELISA), standard virus isolation techniques, and various immunohistochemical assays.

Viral Potency Assays

One of the major obstacles to licensure for a given vaccine is often the development of a suitable potency test. Historically, BVDV potency testing has been conducted according to Supplemental Assay Method for the Titration of Bovine Viral Diarrhea Virus in Vaccine (SAM 101). Methods such as SAM101 utilize monospecific, neutralizing antiserum to neutralize the BHV, $PI_3$ and BRSV fractions prior to inoculation of a susceptible cell line. The cultures are observed for Cytopathic Effect (CPE), and then direct Fluorescence Antibody (FA) and/or Indirect FA (IFA) staining is used to determine if a particular well (dilution) is positive or negative for BVDV Type 1 or Type 2. A titer is then calculated based on the wells that are determined to be positive for CPE/FA.

Conventional methods such as these, however, are not well suited for differentiating between the subgenotypes of BVDV, primarily because existing antibodies for BVDV-1a, BVDV-1b and BVDV-2 lack the specificity required to accurately discriminate individual titers amongst these genotypes and subgenotypes.

This problem can be overcome by exploiting differences that exist in the 5'-untranslated region of the *pestivirus* genome. These differences have been used to segregate pestiviruses into genotypes and subgenotypes (Paton, 1995; and Hofmann et al., 1994). Ridpath and Bolin (1998) reported a polymerase chain reaction (PCR) method for differentiating BVDV-1a, BVDV-1b and BVDV-2. Reverse transcription-quantitative PCR(RT-qPCR) assays have become increasingly common in human biologics, being used to determine potency of measles virus (Schalk et al., 2004); adenovirus based vaccines (Wang et al., 2005), rotavirus vaccines (Ranheim et al., 2006), and trivalent mumps-measles-rubella (MMR) vaccines (Schalk et al., 2005). Each of the aforementioned references is specifically incorporated herein in its entirety by express reference thereto.

In co-pending U.S. Provisional Patent Application No. 61/427,361, entitled "Bovine Viral Diarrhea Virus Type 1b Vaccine Compositions and Methods" (filed concurrently herewith, and specifically incorporated herein in its entirety by express reference thereto), the present inventors reported the development of a modified genetically-based assay protocol useful in obtaining direct viral quantitation (i.e., "potency") of each individual viral component in a multivalent vaccine. The invention replaces conventional FA/IFA assays (such as those described in the current SAM 101 assay) with an RT-qPCR assay to determine the presence or absence of particular virus species, types, or subtypes in individual assay wells (i.e., dilutions).

The potency tests for the individual components of a multivalent vaccine, such as the hexavalent MLV vaccine described herein can also be made more objective by substituting RT-qPCR/qPCR analysis of individual wells for visual observation of CPE. For example, the observation of CPE in viral titration assays can be rather subjective, and is often considered to be the source of differences in MLV vaccine titers between testing facilities. By increasing the objectivity of the assay, however, the reproducibility between laboratories should also increase.

Potency testing for $PI_3$ may be conducted using a modified Supplemental Assay Method for the Titration of Parainfluenza 3 Virus Vaccines (MVSAM102.01). Potency testing for BRSV may be conducted using a modified Supplemental Assay Method for Titration of Bovine Respiratory Syncytial Virus in Vaccines (MVSAM0129.01). These assays are modified by substituting real-time qPCR analysis of individual wells for visual observation of CPE. Titration of the BHV fraction is conducted using a modified Supplemental Assay Method for the Titration of Infectious Bovine Rhinotracheitis Virus in Vaccines (MVSAM0105.01). In this assay, a 96-well format can be used instead of the standard 6-well format, in order to standardize the assays for multivalent vaccine analysis. Importantly, this protocol includes substituting qPCR analysis of individual wells for visual observation and counting of BHV plaques to provide a more accurate and robust assay.

Nucleic Acid Amplification

Nucleic acid, used as a template for amplification, may be isolated from viruses or cells according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to the viral-specific polynucleotides (or to conserved flanking regions) are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from eight or ten to forty or so base pairs (bp) in length, but longer or shorter sequences may be employed in certain embodiments. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals.

A number of template dependent processes are available to amplify the marker sequences present in a given template sample. One of the best-known amplification methods is the polymerase chain reaction (PCR), which is described in detail in U.S. Pat. Nos. 4,683,195, 4,683,202 and 4,800,159 (each of which is incorporated herein by reference in its entirety).

Briefly, in PCR™, two primer sequences are prepared that are complementary to regions on opposite complementary strands of the marker sequence. An excess of deoxynucleoside triphosphates is added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al. (1989). Alternative methods for reverse transcription utilize thermostable, RNA-dependent DNA polymerases.

Methods based on ligation of two (or more) oligonucleotides in the presence of nucleic acid having the sequence of the resulting "di-oligonucleotide," thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (see e.g., Sambrook et al., (1989), which is specifically incorporated herein in its entirety by express reference thereto.

Alternatively, chromatographic techniques may be employed to effect separation of the amplification products and/or of the hybridized amplification products:labeled probe duplexes. There are many kinds of chromatography that may be used in connection with analysis of the amplification products the present invention, including, without limitation, adsorption, partition, ion exchange chromatograph, molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In certain embodiments, visualization may be achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern hybridization analysis ("blotting") with a suitably-labeled oligonucleotide detection probe. The techniques involved in Southern blotting are well known to those of skill in the art and can be found in many standard books on molecular protocols. See Sambrook et al. (1989). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721 (specifically incorporated herein in its entirety by express reference thereto), which discloses an apparatus and method for the automated electrophoresis and transfer of nucleic acids. The apparatus permits electrophoresis and blotting without external manipulation of the gel and is ideally suited to carrying out methods according to the present invention.

Polynucleotide Amplification Kits

The present invention also provides kits for amplifying viral-derived nucleic acids, and in particular, nucleic acids specific for one or more particular strains, types, or subtypes of BVDV, including without limitation, BVDV-1a, BVDV-1b, and BVDV-2. Such kits typically comprise two or more components necessary for amplifying one or more viral nucleic acids from a population of polynucleotides. For example, one container within a kit may contain a first primer, while a second container within the kit may comprise a second primer. A third container within the kit may contain one or more hybridization and/or detection probes, and/or one or more reagents for labeling one or more such detection probes. In addition, the kits of the invention may also comprise instructions for use, e.g., instructions for using the primers in amplification and/or detection reactions as described herein, as well as one or more fluorescent molecule(s), or other reagents as may be necessary, including for example, but not limited to, buffers enzymes, polymerases, RNAses and such like.

Kits for Detection and Quantitation of Viral-Specific Nucleotides

Diagnostic kits represent another aspect of the invention. Such kits may also comprise one or more distinct container means within the kit for the probes, primers, fluorescent labels, or reaction buffers, polymerases, etc. The kit may also further comprise instructions for using the compositions comprised within the kit in one or more polymerase chain reaction-based methodologies, including, without limitation, PCR, qPCR, RT-PCR, RT-PCR/FRET, and the like. Instructions may also be provided for the use of the reagents contained within the kit for the detection of one or more strains, types, or subtypes or a virus, such as BVDV (including, without limitation, BVDV-1a, BVDV-1b, and BVDV-2) or one or more additional mammalian viral pathogens such as, without limitation, BHV-1, PI$_3$, BRSV, and the like in a sample suspected of containing such one or more viral-specific polynucleotides. In certain embodiments, the diagnostic assay kits of the present invention may also preferably comprise instructions for using the items contained within such kits in a PCR, qPCR, RT-PCR, RT-PCR/FRET assay as described herein, including, for example, real-time qPCR.

Either of the aforementioned kits may further optionally include one or more "positive" or "negative" control agent(s) (whether labeled or unlabeled), for use in preparing a standard curve for the detection assay. The components of the kits may be packaged in conventional methods, including, for example, in aqueous media, or as dried, freeze-dried, or lyophilized components. The container means of the kits will generally include at least one vial, test tube, flask, bottle, syringe or other container, into which the components of the assay may be placed, and preferably, suitably dispensed into one or more aliquot(s). Where an additional component is provided, the kit will also generally contain a second, third or other additional container into which this component may be placed. The kits may also include other diagnostic reagents for use in identifying, quantifying, speciating, or characterizing the MLVs contained within a sample such as a polyvalent vaccine formulation. The kits of the present invention will also typically include a means for containing the probe(s), primer(s), and/or assay reagent(s) in close confinement for commercial sale. Such containers may include, for example, one or more injection or blow-molded plastic container(s) into which the desired reagent vessels (e.g., vials, test tubes, syringes, etc.) are retained.

Exemplary Definitions

In accordance with the present invention, polynucleotides, nucleic acid segments, nucleic acid sequences, and the like, include, but are not limited to, DNAs (including e.g., and not limited to genomic or extragenomic DNAs), genes, peptide nucleic acids (PNAs) RNAs (including e.g., but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "PCR reagents" refers to the chemicals, apart from the target nucleic acid sequence, needed to perform a polymerase chain reaction assay. These chemicals generally include five categories of components: (a) an aqueous buffer; (b) a water-soluble magnesium salt; (c) deoxyribonucleotide triphosphates (dNTPs); (d) forward and reverse oligonucleotide primer pairs; and (e) a thermostable DNA polymerase (i.e., a DNA polymerase that can tolerate temperatures between about 80 and about 100° C. for at least about 10 min without losing more than about half of its enzymatic activity. The four conventional dNTPs are thymidine triphosphate (dTTP), deoxyadenosine triphosphate (dATP), deoxycitidine triphosphate (dCTP) and deoxyguanosine triphosphate (dGTP), although they may be supplemented or replaced in the PCR reaction by one or more dNTPs containing base analogs that base pair in Watson-Crick fashion in a manner similar to one of the conventional bases (e.g., deoxyuridine triphosphate [dUTP] and the like).

The term "oligonucleotide" as used herein includes linear oligomers of natural or modified monomers or linkages, including deoxyribonucleotides, ribonucleotides, and the like, that are capable of specifically binding to a target nucleic acid via an orderly pattern of monomer-to-monomer interactions (e.g., via Watson-Crick base pairing or the like). The monomers are typically linked via phosphodiester (or equivalent) bonds to form oligonucleotides that range in size from a few monomeric units to several tens of monomeric units. Throughout the disclosure, whenever an oligonucleotide is represented by a sequence of letters (e.g., "TTACGCAG"), it will be understood that the nucleotides are presented in 5'→3' order, reading left to right. In such representations, "A" is understood to mean adenosine (or in the case of DNA, deoxyadenosine), while "C," "G," "T," and "U," denote cytidine/deoxycytidine, guanosine/deoxyguanosine, deoxythymidine, and uridine, respectively. Analogs of phosphodiester linkages include, without limitation, phosphorothioate, phosphoranilidate, phosphoramidate, and the like.

The terms "substantially corresponds to," "substantially homologous," or "substantial identity" as used herein denotes a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more oligo- or polynucleotide sequences, the reference sequence will typically comprise at least about 10-15 nucleotides, more typically at least about 16 to 25 nucleotides, and even more typically at least about 26-35 nucleotides, at least about 40 nucleotides, at least about 45 nucleotides, at least about 50 nucleotides, or at least about 60, 70, 80, 90, or even at least about 100 or so nucleotides.

Preferably, when highly homologous fragments are desired, the percent identity between the two sequences (often referred to as "target" and "probe" sequences) will be at least about 80% identical, preferably at least about 85% identical, and more preferably at least about 90% identical, at least about 92% identical, at least about 93% identical, at least about 94% identical, or even at least about 95%, 96%, 97%, 98%, or 99% or higher. The percentage of homology or percentage of identity between 2 or more oligo- or polynucleotide sequences may readily be determined by one of skill in the art, using one or more of the standard sequence comparison algorithms, such as, e.g., the FASTA program analysis described by Pearson and Lipman (1988).

The term "naturally-occurring" as used herein as applied to an object refers to the fact that an object can be found in nature. For example, a polypeptide or polynucleotide sequence that can be isolated from a source in nature, and which has not been intentionally modified by the hand of man, is a "naturally-occurring" sequence.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, 2, 3, 4, 5, 6, 7, 8, 9, or 10 base mismatches throughout the complementary portion of the sequence.

Substantially complementary oligonucleotide sequences will be greater than about 80 percent complementary, greater than about 85 percent complementary, greater than about 90 percent complementary, or even greater than about 95 percent complementary (or "% exact-match") to the corresponding target nucleic acid sequence to which the oligonucleotide specifically binds, and will, more preferably be greater than about 96% or higher complementary to the corresponding nucleic acid sequence to which the oligonucleotide specifically binds.

In certain aspects, as described above, it will be desirable to have even more substantially complementary oligonucleotide sequences for use in the practice of the invention, and in such instances, the oligonucleotide sequences will be greater than about 96%, 97%, 98%, 99%, or even 100% complementary to all or a portion of the target nucleic acid sequence to which the designed oligonucleotide probe or primer specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch. Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov et al., (2) a penalty of 3.0 for each gap and an additional 0.10 penalty for each symbol in each gap; and (3) no penalty for end gaps.

In many instances, it may be desirable for the sequences to be exact matches, i.e., be completely complementary to the sequence to which the oligonucleotide specifically binds, and therefore have zero mismatches along the complementary stretch. As such, highly complementary primer or probe sequences will typically bind quite specifically to the target sequence region of the plurality of polynucleotides and will therefore be highly efficient in directing amplification of the target sequence via PCR, qPCR, RT-qPCR, or RT-qPCR/FRET, etc.

"Amplification reaction mixture" refers to an aqueous solution comprising the one or more various reagents necessary to amplify one or more selected target nucleic acid sequence(s). Such mixtures include, without limitation, one or more enzymes, one or more aqueous buffers, one or more salts, one or more target nucleic acid(s), and a plurality of conventional nucleoside triphosphates. Depending upon the context, the mixture can be either a complete or incomplete amplification reaction mixture.

"Amplification reaction" refers to any in vitro method for multiplying a target nucleic acid sequence to produce a population of such sequences. Conventional amplification methods include, but are not limited to, PCR, DNA ligase, Qβ replicase, RNA transcription-based amplification systems, and the like.

As used herein, the term "amplification reagents" refers to the various buffers, enzymes, primers, nucleoside triphosphates (both conventional and unconventional), and probes used to perform the selected amplification reaction.

As used herein, "amplifying" or "amplification" typically refers to an exponential increase in target nucleic acid is being used herein to describe both linear and exponential increases in the numbers of a select target sequence of nucleic acid.

"Bind(s) substantially" refers to complementary hybridization between oligonucleotides and embraces minor mismatches which can be accommodated by reducing the stringency of the hybridization media to achieve the desire priming of the PCR polymerases.

As used herein, "biotinylated" refers to a biotin moiety covalently attached to the 5' end of an oligonucleotide for the purpose of reacting with streptavidin in a detection assay.

In the context of nucleic acids, the terms "bind," "binding," and "bound" refer to the hybridization of two or more nucleic acid sequences through complementary Watson-Crick base pairing.

As used herein, "nucleic acid" refers to a deoxyribonucleotide or ribonucleotide polymer in either single or double stranded form and unless otherwise limited would encompass known analog of natural nucleotides which can function in a similar manner as naturally occurring nucleotides.

A "nucleotide polymerase" is an enzyme capable of catalyzing the synthesis of DNA or RNA from a population of nucleoside triphosphate precursors. In the amplification reactions of this invention the polymerases are template-dependent and typically extend from the 21 end of the polymer being formed. In preferred applications, the employed polymerase is a thermostable polymerase.

As used herein, "primer" or "oligonucleotide primer(s)" refers to an oligonucleotide, whether natural or synthetic, capable of acting as a point of initiation of DNA synthesis under conditions in which synthesis of a primer extension product complementary to a nucleic acid strand is initiated (i.e., in the presence of four different nucleotide triphosphates, and an agent for polymerization, such as a DNA polymerase or reverse transcriptase) in an appropriate buffer and at a suitable temperature. In the context of the invention, a primer is preferably an oligodeoxyribonucleotide, and preferably single-stranded for maximum efficiency in amplification. As known to those of ordinary skill in the art, such primers need not reflect the exact sequence of the target template, but must be sufficiently complementary t the sequence, however, to permit hybridization (i.e., binding) to the template under suitable reaction conditions.

As used herein, a "modified live vaccine" is a vaccine comprising a virus that has been altered, typically by passaging in tissue culture cells, to attenuate its ability to cause disease, but which retains its ability to protect against disease or infection when subsequently administered to an animal.

The term "pathogen" is defined herein as any sort of infectious agent, including e.g., viruses, prions, protozoans, parasites, as well as microbes such as bacteria, yeast, molds, fungi, and the like.

As used herein, the term "individual" (also interchangeably referred to as "host," "subject," "recipient," "patient," etc.) refers to any animal that can receive one or more of the pharmaceutical compositions or vaccine formulations disclosed herein. Preferably, the subject is a vertebrate animal, which is intended to denote any animal species (and preferably, a mammalian species). In certain embodiments, the individual is preferably any mammalian host, including but not limited to, non-human primates, bovines, canines, caprines, cavines, corvines, epines, equines, felines, hircines, lapines, leporines, lupines, ovines, porcines, racines, vulpines, and the like, including livestock, zoological specimens, exotics, as well as companion animals, pets, and any animal under the care of a veterinary practitioner.

As used herein, the term "vaccine" refers to a composition or formulation that contains an immunogenic composition of the present invention in a form that is capable of being administered to a vertebrate, and preferably to an animal such as a mammal Typically, vaccines of the present invention will include one or more of the immunogenic compositions (including one or more modified, live virus particles or pluralities thereof) disclosed herein, formulated for administration to an animal in need thereof. Such compositions may be of any suitable formulation, including, without limitation, those prepared in an aqueous vehicle, as well as those in frozen, freeze-dried, lyophilized, or dehydrated form that are then subsequently rehydrated or suspended in a conventional pharmaceutically-acceptable vehicle (e.g., sterile saline or a similar buffered aqueous solution) prior to administration. In such forms, the vaccine compositions of the present invention can be manufactured in convenient single or multiple-dose aliquots that may readily be employed in one or more of the methods or vaccination regimens disclosed herein to prevent, manage or otherwise treat one or more conditions or one or more symptoms of viral and/or microbial infection in a susceptible animal.

The term "e.g.," as used herein, is used merely by way of example, without any limitation intended; as such, it should not be construed as referring only to those items explicitly enumerated in the specification.

A "target sequence" or "target nucleotide sequence" as used herein includes any nucleotide sequence to which one of said primer sequences hybridizes under conditions that allow an enzyme having polymerase activity to elongate the primer sequence, and thereby replicate the complementary strand.

A nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

A "primer" or "primer sequence" may include any nucleic acid sequence or segment that selectively hybridizes to a complementary template nucleic acid strand ("target sequence") and functions as an initiation point for the addition of nucleotides to replicate the template strand. Primer sequences of the present invention may be labeled or contain other modifications which allow the detection and/or analysis of amplification products. In addition to serving as initiators for polymerase-mediated duplication of target DNA sequences, primer sequences may also be used for the reverse transcription of template RNAs into corresponding DNAs.

As used herein, "fluorescence resonance energy transfer pair" or "FRET pair" refers to a pair of fluorophores comprising a donor fluorophore and acceptor fluorophore, wherein the donor fluorophore is capable of transferring resonance energy to the acceptor fluorophore. In preferred fluorescence resonance energy transfer pairs, the absorption spectrum of the donor fluorophore does not substantially overlap the absorption spectrum of the acceptor fluorophore. As used herein, "a donor oligonucleotide probe" refers to an oligonucleotide that is labeled with a donor fluorophore of a FRET pair. As used herein, "an acceptor oligonucleotide probe" refers to an oligonucleotide that is labeled with an acceptor fluorophore of a FRET pair. As used herein, a "FRET oligonucleotide pair" will typically comprise an "anchor" or "donor" oligonucleotide probe and an "acceptor" or "sensor" oligonucleotide probe, and such a pair forms a FRET relationship when the donor oligonucleotide probe and the acceptor oligonucleotide probe are both hybridized to their complementary target nucleic acid sequences. Acceptable fluorophore pairs for use as FRET pairs are well known to those skilled in the art and include, but are not limited to, fluorescein/rhodamine, phycoerythrin/Cy7, fluorescein/Cy5, fluorescein/Cy5.5, fluorescein/LC Red 640, and fluorescein/LC Red 705. In accordance with long standing patent law convention, the words "a" and "an" when used in this application, including the claims, denotes "one or more."

EXAMPLE

The following example is included to demonstrate illustrative embodiments of the invention. It should be appreciated by those of ordinary skill in the art that the techniques disclosed in the example that follows represent techniques discovered to function well in the practice of the invention, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Potency Assay Protocol for Components of Multifactorial Vaccines

The present example demonstrates use of a quantitative (real-time) polymerase chain reaction (qPCR) assay to successfully determine the potency of individual viral components of a multivalent modified, live virus (MLV) vaccine.

In the inventors' co-pending U.S. Provisional Patent Application No. 61/427,361, the present inventors have developed a six-way (i.e., hexavalent) modified, live virus (MLV) vaccine effective against BRDC and shipping fever. The present example describes assays useful in quantitating the individual viral components of such a vaccine. The inventors show that the assay is particularly advantageous over existing methodologies in determining the individual potencies of genetically related strains in a multivalent (i.e., polyvalent or multicomponent) vaccine. Using the hexavalent MLV BRDC vaccine as a model, the inventors have demonstrated that the assay is effective in differentiating between and quantitating the potencies of individual vaccine components, even when the vaccine contained three subgenotypes of a single type of virus. Such assay offers new and more reliable methods for accurately quantitating the presence of BVDV-1a, BVDV-1b, and BVDV-2 in polyvalent vaccine formulations.

Materials and Methods

Cell Culture

All cultures are prepared using conventional techniques and supplies as described by Freshney (1987). The TVL-Bovine Kidney Cell Line, which exhibit a typical epithelial like morphology in culture, is used for all culture assays.

The BVDV-1b Master Seed culture (designated "TVL BVDV1b MS Apr. 27, 2007 DW3-095" in Applicants' copending U.S. provisional patent application No. 61/427,361) has been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action. The subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the finishing of a sample of the deposit, and in any case, for a period of at least 30 (thirty) years after the date of deposit or for the enforceable life of any patent which may issue disclosing the deposited culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it. A deposit of TVL BVDV1b MS Apr. 27, 2007 DW3-095 virus was entered into the permanent collection of the Patent Depository of the American Type Culture Laboratory, located at 10801 University Blvd., Manassas, Va., 20110-2209, USA, on Dec. 21, 2010 under the terms of the Budapest Treaty, whereupon it was assigned accession number ATCC PTA-11553 by the repository.

Specificity of Primer/Probe Sets

RNA is extracted from viral fluids from each of the following United States Department of Agriculture (USDA)-approved viral seeds: BVDV-1a (Singer strain), BVDV-1b (TGAC Strain), BVDV-2 (125), $PI_3$ (Reisinger SF-4), and BRSV (N375) (no extraction process is performed on BHV-1 [Cooper strain] since it is a DNA virus). Extractions are performed using RNAqueous®-4PCR (Ambion; Austin, Tex., USA).

Each of the RNA viral samples is used as template (sample) in separate RT-qPCR reactions for each of the six primer/probe sets using TaqMan® one-step RT-PCR chemistry. The DNA virus (BHV-1) is also used as template (sample) in separate qPCR reactions with each of the six primer/probe sets described above. Analysis of the BRSV primer/probe set against all six viral fractions of the hexavalent vaccine indicate there is no cross-reactivity for each of the primer/probe sets with any of the other viral fractions.

qPCR Assays qPCR assays are conducted using an Applied Biosystems 7500 Real-Time PCR System.

Oligonucleotide Primers and Labeled Molecular Probes

The following custom TaqMan® Probes and virus-specific forward and reverse primer pairs were fabricated by Applied Biosystems (Foster City, Calif., USA).

```
BVDV-1b (first):
Forward primer:
                              (SEQ ID NO: 1)
5'-CACCCTATCAGGCTGTATTCATAGC-3';

Reverse primer:
                              (SEQ ID NO: 2)
5'-TGCCCACAGCACATCTTAACC-3';
and BVDV-1b Detection probe:
                              (SEQ ID NO: 3)
5'-TCACCTGGACGACCC-3'.

BVDV-1b (second):
Second Forward primer:
                              (SEQ ID NO: 19)
5'-GTCGTCCAGGTGAAAACGGT-3';

Second Reverse primer:
                              (SEQ ID NO: 20)
```

```
5'-GTCGTCCAGGTGAAAACGGT-3';
and

Second BVDV-1b Detection probe:
                              (SEQ ID NO: 21)
5'-GTCGTCCAGGTGAAAACGGT-3'.
```

While BVDV-1b (first) provided acceptable results, BVDV-1b (second) displayed better results.

```
BRSV:
Forward primer:
                              (SEQ ID NO: 4)
5'-GCAATGCTGCAGGACTAGGTATAAT-3';

(SEQ ID NO: 5)
Reverse primer:
5'-ACACTGTAATTGATGACCCCATTCT-3';
and

BRSV Detection probe:
                              (SEQ ID NO: 6)
5'-AAGACTTGTATGATGCTGCCAA-3'.

BVDV-1a:
Forward primer:
                              (SEQ ID NO: 7)
5'-GGTCGCCCAGGTAAAAGCA-3';

Reverse primer:
                              (SEQ ID NO: 8)
5'-GCCTCTGCAGCACCCTATCA-3';
and BVDV-1a Detection probe:
                              (SEQ ID NO: 9)
5'-AACCGACTGTTACGAATAC-3'.

BVDV-2:
Forward primer:
                              (SEQ ID NO: 10)
5'-GCTAGCCATGCCCTTAGTAGGAC-3';

Reverse primer:
                              (SEQ ID NO: 11)
5'-GACGAGTCCCCTGTACTCAGG-3';
and BVDV-2 Detection probe:
                              (SEQ ID NO: 12)
5'-CAGTGAGTCCATTGGATGG-3'.

PI3:
Forward primer:
                              (SEQ ID NO: 13)
5'-GGAGACCAAGACCAAGGAGATG-3';

Reverse primer:
                              (SEQ ID NO: 14)
5'-CGTCTGCCCATGCATAAGG-3';
and PI3 Detection probe:
                              (SEQ ID NO: 15)
5'-ACCTCGGTCATCCATAG-3'.

BHV-1:
Forward primer:
                              (SEQ ID NO: 16)
5'-CCATGTTAGCGCTCTGGAACC-3';

Reverse primer:
                              (SEQ ID NO: 17)
5'-CGTCTTTACGGTCGACGACTCC-3';
and BHV-1 Detection probe:
                              (SEQ ID NO: 18)
5'-ACGGACGTGCGCGAA-3'.
```

Potency Assay for Monovalent Vaccines

Protocols for each of the following assays utilize Applied Biosystems 7500 Comparative Threshold Cycle ($C_T$) methodology to determine if an individual well of a titration plate contains a greater amount of virus than the equivalent reference well. Most viral samples contain some non-viable viral particles that could be detected by the PCR assay, thus giving potentially false-positive results. This issue is resolved by the use of a reference plate without cells. The sample is diluted in the reference plate exactly as it is in the assay plate but without cells as to eliminate the possibility for viral replication. The reference plate is used to generate as baseline or background $C_T$ value for each of the wells in each assay. If a well on the assay plate has a higher $C_T$ value than the corresponding background well, viral replication has occurred and the well is considered positive. If no $C_T$ value is determined for a well, or the $C_T$ value is equivalent to the background $C_T$ value, then the well is considered negative.

Potency Assay for Multivalent Vaccines

A pilot serial of the IBR/BVDV-1a, -1b, -2/PI$_3$/RSV hexavalent vaccine, modified live virus, was prepared as described herein. Briefly, BHV-1 (Cooper strain), BVDV-1a (Singer strain), BVDV-1b (TGAC Strain), BVDV-2 (125), PI$_3$ (Reisinger SF-4), and BRSV (N375) were propagated in the TVL-BK cell line (20$^{th}$ pass). Individual fractions were harvested at the 10$^{th}$ passage and blended together into the six-way product. A potency test of for each fraction of the 6-way vaccine may be conducted as described herein with the addition of appropriate neutralizing antisera. The TCID$_{50}$ of each viral fraction is determined based on CPE/FA/IFA results and compared to those based on RT-qPCR/qPCR.

BVDV-1a, BVDV-1b, and BVDV-2 Potency Tests

Monovalent BVDV-1a, BVDV-1b and BVDV-2 samples may be titered separately according to Supplemental Assay Method for the Titration of Bovine Viral Diarrhea Virus in Vaccine (SAM 101). Briefly, the assay is conducted in duplicate with one of the plates being used for titer calculation based on CPE and/or FA/IFA as described. The other plate is used to determine a titer based on RT-qPCR. A cell-deficient reference plate is included as described above for each of the viruses.

$PI_3$ Potency Test

Potency testing for $PI_3$ is conducted in duplicate with one of the plates being used for titer calculation based on CPE. The other plate is used to determine a titer based on the comparative $C_T$ values of $PI_3$ as determined by RT-qPCR. A cell-deficient reference plate is included as described above.

BRSV Potency Test

Potency testing for BRSV is conducted in duplicate with one of the plates being used for titer calculation based on CPE as described above, with the remaining plate being used to determine a titer based on the comparative $C_T$ values of BRSV as determined by RT-qPCR. As discussed above, a cell-deficient reference plate is also included in the assay.

BHV Potency Test

Potency testing for BHV is conducted in a 96-well format, by substituting qPCR analysis of individual wells for conventional visual observation and counting of plaques. The assay is performed in duplicate, with one of the plates being used for titer calculation based on presence or absence of CPE in an individual well (dilution), while the remaining plate is used to calculate a titer based on the comparative $C_T$ values of BHV as determined by QPCR. A cell-deficient reference plate is included as described above.

Test Results
Results from the above tests are provided below.

TABLE 1

Known virus samples from each of the six viruses under investigation were run against an RT-PCR BVD 1a probe-primer set (1A pp). The BVD 1a probe-primer set had no cross reactivity with any of the other viruses under investigation.

| Well | Sample Name | Target | Reporter | Quencher | $C_T$ | $C_T$ Mean |
|---|---|---|---|---|---|---|
| A7 | BHV nd and 1A pp | BVD 1a | FAM | NFQ-MGB | Undetermined | Undetermined |
| A8 | 1A nd and 1A pp | BVD 1a | FAM | NFQ-MGB | 19.09957 | 19.09957 |
| A9 | PI3 nd and 1A pp | BVD 1a | FAM | NFQ-MGB | Undetermined | Undetermined |
| A10 | 1B nd and 1A pp | BVD 1a | FAM | NFQ-MGB | Undetermined | Undetermined |
| A11 | BVD2 nd and 1A pp | BVD 1a | FAM | NFQ-MGB | Undetermined | Undetermined |
| A12 | BRSV nd and 1A pp | BVD 1a | FAM | NFQ-MGB | Undetermined | Undetermined |
| D3 | 1A + CONTROL | BVD 1a | FAM | NFQ-MGB | 20.24967 | 20.24967 |
| D4 | 1A − CONTROL | BVD 1a | FAM | NFQ-MGB | Undetermined | Undetermined |

(nd = no dilution, pp = probe-primer set)

TABLE 2

Log dilution of BVD 1a (1A) with known $TCID_{50}$ with its corresponding $C_T$ scores from reaction with an RT-PCR BVD 1a probe-primer set and the extrapolated $TCID_{50}$ values for each dilution.

| Well | Sample Name | Target | Reporter | Quencher | $C_T$ | $C_T$ Mean | $TCID_{50}$ |
|---|---|---|---|---|---|---|---|
| A8 | 1A nd and 1A pp | BVD 1a | FAM | NFQ-MGB | 19.09957 | 19.09957 | 7.79 |
| E8 | 1A $10^{-1}$ | BVD 1a | FAM | NFQ-MGB | 25.53863 | 25.53863 | 6.79 |
| E9 | 1A $10^{-2}$ | BVD 1a | FAM | NFQ-MGB | 29.94803 | 29.94803 | 5.79 |
| E10 | 1A $10^{-4}$ | BVD 1a | FAM | NFQ-MGB | 35.1481 | 35.1481 | 3.79 |
| E11 | 1A $10^{-6}$ | BVD 1a | FAM | NFQ-MGB | Undetermined | Undetermined | 1.79 |
| E12 | 1A $10^{-8}$ | BVD 1a | FAM | NFQ-MGB | Undetermined | Undetermined | 0.79 |

(nd = no dilution, pp = probe-primer set)

TABLE 3

Known virus samples from each of the six viruses under investigation were run against an RT-PCR BRSV probe-primer set (pp). The BRSV probe-primer set had no cross reactivity with any of the other viruses under investigation.

| Well | Sample Name | Target | Reporter | Quencher | $C_T$ | $C_T$ Mean |
|---|---|---|---|---|---|---|
| C6 | BHV nd and BRSV pp | BRSV | FAM | NFQ-MGB | Undetermined | Undetermined |
| C7 | 1A nd and BRSV pp | BRSV | FAM | NFQ-MGB | Undetermined | Undetermined |
| C8 | PI3 nd and BRSV pp | BRSV | FAM | NFQ-MGB | Undetermined | Undetermined |
| C9 | 1B nd and BRSV pp | BRSV | FAM | NFQ-MGB | Undetermined | Undetermined |
| C10 | BVD2 nd and BRSV pp | BRSV | FAM | NFQ-MGB | Undetermined | Undetermined |
| C11 | BRSV nd and BRSV pp | BRSV | FAM | NFQ-MGB | 19.72052 | 19.72052 |
| C12 | BRSV + CONTROL | BRSV | FAM | NFQ-MGB | 21.971 | 21.971 |
| D1 | BRSV − CONTROL | BRSV | FAM | NFQ-MGB | Undetermined | Undetermined |

(nd = no dilution, pp = probe-primer set)

TABLE 4

Log dilution of BRSV with known $TCID_{50}$ with its corresponding $C_T$ scores from reaction with an RT-PCR BRSV probe-primer set and the extrapolated $TCID_{50}$ values for each dilution.

| Well | Sample Name | Target | Reporter | Quencher | $C_T$ | $C_T$ Mean | $TCID_{50}$ |
|---|---|---|---|---|---|---|---|
| C11 | BRSV nd and BRSV pp | BRSV | FAM | NFQ-MGB | 19.72052 | 19.72052 | 5.79 |
| H8 | BRSV $10^{-1}$ | BRSV | FAM | NFQ-MGB | 26.95523 | 26.95523 | 4.79 |
| H9 | BRSV $10^{-2}$ | BRSV | FAM | NFQ-MGB | 29.32718 | 29.32718 | 3.79 |
| H10 | BRSV $10^{-4}$ | BRSV | FAM | NFQ-MGB | 36.95991 | 36.95991 | 1.79 |
| H11 | BRSV $10^{-6}$ | BRSV | FAM | NFQ-MGB | Undetermined | Undetermined | NA |
| H12 | BRSV $10^{-8}$ | BRSV | FAM | NFQ-MGB | Undetermined | Undetermined | NA |

(nd = no dilution, pp = probe-primer set)

TABLE 5

Known virus samples from each of the six viruses under investigation were run against an RT-PCR BVD 1b probe-primer set (1B pp). The BVD 1b probe-primer set had no cross reactivity with any of the other viruses under investigation.

| Well | Sample Name | Target | Reporter | Quencher | $C_T$ | $C_T$ Mean |
|---|---|---|---|---|---|---|
| H1 | BHV + and 1B pp | BVD 1b | FAM | NFQ-MGB | Undetermined | Undetermined |
| H2 | 1A + and 1B pp | BVD 1b | FAM | NFQ-MGB | Undetermined | Undetermined |
| H3 | PI3 + and 1B pp | BVD 1b | FAM | NFQ-MGB | Undetermined | Undetermined |
| H7 | 1B nd and 1B pp | BVD 1b | FAM | NFQ-MGB | Undetermined | 18.81768 |
| H5 | BVD2 + and 1B pp | BVD 1b | FAM | NFQ-MGB | Undetermined | Undetermined |
| H6 | BRSV + and 1B pp | BVD 1b | FAM | NFQ-MGB | Undetermined | Undetermined |
| H4 | 1B + CONTROL | BVD 1b | FAM | NFQ-MGB | 20.74105 | 20.74105 |
| C12 | 1B − CONTROL | BVD 1b | FAM | NFQ-MGB | Undetermined | Undetermined |

(nd = no dilution, pp = probe-primer set, + = positive control)

TABLE 6

Log dilution of BVD 1b (1B) with known $TCID_{50}$ with its corresponding $C_T$ scores from reaction with an RT-PCR BVD 1b probe-primer set and the extrapolated $TCID_{50}$ values for each dilution.

| Well | Sample Name | Target | Reporter | Quencher | $C_T$ | $C_T$ Mean | $TCID_{50}$ |
|---|---|---|---|---|---|---|---|
| H7 | 1B nd and 1B pp | BVD 1b | FAM | NFQ-MGB | 18.81769 | 18.81769 | 7.79 |
| H8 | 1B $10^{-1}$ | BVD 1b | FAM | NFQ-MGB | 27.91738 | 27.91738 | 6.79 |
| H9 | 1B $10^{-2}$ | BVD 1b | FAM | NFQ-MGB | 33.86901 | 33.86901 | 5.79 |
| H10 | 1B $10^{-4}$ | BVD 1b | FAM | NFQ-MGB | Undetermined | Undetermined | 3.79 |
| H11 | 1B $10^{-6}$ | BVD 1b | FAM | NFQ-MGB | Undetermined | Undetermined | 1.79 |
| H12 | 1B $10^{-8}$ | BVD 1b | FAM | NFQ-MGB | Undetermined | Undetermined | 0.79 |

(nd = no dilution, pp = probe-primer set)

TABLE 7

Known virus samples from each of the six viruses under investigation were run against an RT-PCR PI3 probe-primer set. The PI3 probe-primer set had no cross reactivity with any of the other viruses under investigation.

| Well | Sample Name | Target | Reporter | Quencher | $C_T$ | $C_T$ Mean |
|---|---|---|---|---|---|---|
| B1 | BHV nd and PI3 pp | PI3 | FAM | NFQ-MGB | Undetermined | Undetermined |
| B2 | 1A nd and PI3 pp | PI3 | FAM | NFQ-MGB | Undetermined | Undetermined |
| B3 | PI3 nd and PI3 pp | PI3 | FAM | NFQ-MGB | 11.23717 | 11.23717 |
| B4 | 1B nd and PI3 pp | PI3 | FAM | NFQ-MGB | Undetermined | Undetermined |
| B5 | BVD2 nd and PI3 pp | PI3 | FAM | NFQ-MGB | Undetermined | Undetermined |
| B6 | BRSV nd and PI3 pp | PI3 | FAM | NFQ-MGB | Undetermined | Undetermined |
| D5 | PI3 + CONTROL | PI3 | FAM | NFQ-MGB | 19.16233 | 19.16233 |
| D6 | PI3 − CONTROL | PI3 | FAM | NFQ-MGB | Undetermined | Undetermined |

(nd = no dilution, pp = probe-primer set)

TABLE 8

Log dilution of PI3 with known $TCID_{50}$ with its corresponding $C_T$ scores from reaction with an RT-PCR PI3 probe-primer set and the extrapolated $TCID_{50}$ values for each dilution.

| Well | Sample Name | Target | Reporter | Quencher | $C_T$ | $C_T$ Mean | $TCID_{50}$ |
|---|---|---|---|---|---|---|---|
| B3 | PI3 nd and PI3 pp | PI3 | FAM | NFQ-MGB | 11.23717 | 11.23717 | 9.44 |
| F1 | PI3 $10^{-1}$ | PI3 | FAM | NFQ-MGB | 21.23889 | 21.23889 | 8.44 |
| F2 | PI3 $10^{-2}$ | PI3 | FAM | NFQ-MGB | 26.39993 | 26.39993 | 7.44 |
| F3 | PI3 $10^{-4}$ | PI3 | FAM | NFQ-MGB | 30.55147 | 30.55147 | 5.44 |
| F4 | PI3 $10^{-5}$ | PI3 | FAM | NFQ-MGB | 34.95575 | 34.95575 | 4.44 |
| F5 | PI3 $10^{-7}$ | PI3 | FAM | NFQ-MGB | Undetermined | Undetermined | 2.44 |
| F6 | PI3 $10^{-8}$ | PI3 | FAM | NFQ-MGB | Undetermined | Undetermined | 1.44 |
| F7 | PI3 $10^{-10}$ | PI3 | FAM | NFQ-MGB | Undetermined | Undetermined | NA |

(nd = no dilution, pp = probe-primer set)

TABLE 9

Known virus samples from each of the six viruses under investigation were run against an RT-PCR BHV probe-primer set. The BHV probe-primer set had no cross reactivity with any of the other viruses under investigation.

| Well | Sample Name | Target | Reporter | Quencher | $C_T$ | $C_T$ Mean |
|---|---|---|---|---|---|---|
| A1 | BHV nd and BHV pp | BHV | FAM | NFQ-MGB | 14.87263107 | 14.87263 |
| A2 | 1A nd and BHV pp | BHV | FAM | NFQ-MGB | Undetermined | Undetermined |
| A3 | PI3 nd and BHV pp | BHV | FAM | NFQ-MGB | Undetermined | Undetermined |
| A4 | 1B nd and BHV pp | BHV | FAM | NFQ-MGB | Undetermined | Undetermined |
| A5 | BVD2 nd and BHV pp | BHV | FAM | NFQ-MGB | Undetermined | Undetermined |
| A6 | BRSV nd and BHV pp | BHV | FAM | NFQ-MGB | Undetermined | Undetermined |
| D1 | BHV + CONTROL | BHV | FAM | NFQ-MGB | 11.92034817 | 11.92035 |
| D2 | BHV – CONTROL | BHV | FAM | NFQ-MGB | Undetermined | Undetermined |

(nd = no dilution, pp = probe-primer set)

TABLE 10

Log dilution of BHV with known $TCID_{50}$ with its corresponding $C_T$ scores from reaction with an RT-PCR BHV probe-primer set and the extrapolated $TCID_{50}$ values for each dilution.

| Well | Sample Name | Target | Reporter | Quencher | $C_T$ | $C_T$ Mean | $TCID_{50}$ |
|---|---|---|---|---|---|---|---|
| A1 | BHV nd and BHV pp | BHV | FAM | NFQ-MGB | 14.87263107 | 14.87263 | 8.32 |
| E1 | BHV $10^{-1}$ | BHV | FAM | NFQ-MGB | 20.99085045 | 20.99085 | 7.32 |
| E2 | BHV $10^{-2}$ | BHV | FAM | NFQ-MGB | 25.22445679 | 25.22446 | 6.32 |
| E3 | BHV $10^{-4}$ | BHV | FAM | NFQ-MGB | 29.45383453 | 29.45383 | 4.32 |
| E4 | BHV $10^{-5}$ | BHV | FAM | NFQ-MGB | 36.95075989 | 36.95076 | 3.32 |
| E5 | BHV $10^{-7}$ | BHV | FAM | NFQ-MGB | Undetermined | Undetermined | 1.32 |
| E6 | BHV $10^{-8}$ | BHV | FAM | NFQ-MGB | Undetermined | Undetermined | NA |
| E7 | BHV $10^{-10}$ | BHV | FAM | NFQ-MGB | Undetermined | Undetermined | NA |

(nd = no dilution, pp = probe-primer set)

REFERENCES

The following references, to the extent that they provide exemplary procedural or other details supplementary to those set forth herein, are specifically incorporated herein in their entirety by express reference thereto:

U.S. Pat. No. 4,415,732 to Caruthers et al.
U.S. Pat. No. 4,458,066 to Caruthers et al.
U.S. Pat. No. 4,683,195 to Mullis et al.
U.S. Pat. No. 4,683,202 to Mullis et al.
U.S. Pat. No. 4,725,677 to Koster et al.
U.S. Pat. No. 4,973,679 to Caruthers et al.
U.S. Pat. No. 4,980,460 to Molko et al.
U.S. Pat. No. 5,614,388 to Picone et al.
Agrawal et al., *Nucl. Acids Res.*, 18:5419-5423, 1990
Baker, J. C., "The clinical manifestations of bovine viral diarrhea infection," *Vet. Clin. N. Am. Food Anim. Pract.*, 11:425-445, 1995.
Baker, J. C., Werdin, R. E., Ames, T. R., Markham, R. J., and Larson, V. L., "Study on the etiologic role of bovine respiratory syncytial virus in pneumonia of dairy calves," *J. Am. Vet. Med. Assoc.*, 189(1):66-70, 1986.
Barber, D. M., Nettleton, P. F., and Herring, J. A., "Disease in a dairy herd associated with the introduction and spread of bovine diarrhoea virus," *Vet. Rec.*, 117(18):459-464, 1985.
Beaucage and Iyer, *Tetrahedron*, 48:2223-2311, 1992.
Becher, P., Konig, M., Paton, D. J., and Thiel, H. J., "Further characterization of border disease virus isolates: evidence for the presence of more than three species within the genus *pestivirus*," *Virology*, 209(1):200-206, 1995.
Collett, M. S., R. Larson, S. K. Belzer, and E. Retzel, "Proteins encoded by bovine viral diarrhea virus: the gehomic organization of a *pestivirus*," *Virology*, 165(1):200-208, 1988.
Elbers, K., N. Tautz, P. Becher, D. Stoll, T. Rumenapf, and H. J. Thiel, "Processing in the *pestivirus* E2-NS2 region: identification of proteins p7 and E2p7," *J. Virol.*, 70(6):4131-4135, 1996.
Fergen, B. J., "Estimating an Intervention Effect on Outcome Severity," USDA Center for Veterinary Biologics, Ames, Iowa, USA; Personal communication, 2004.
Finney, D. J., "Statistical method in biological assay," 3rd Ed., Charles Griffin and Company Ltd., London, 1978.
Flores, E. F., Ridpath, J. F., Weiblen, R. et al., "Phylogenetic analysis of Brazilian bovine viral diarrhea virus type 2 (BVDB-2) isolates: evidence of subgenotype within BVDV-2," *Virus Res.*, 87:51-60, 2002.
Freshney, R. I., "Culture of Animal Cells, A Manual of Basic Technique," Second Edition, Dept of Medical Oncology, University of Glasgow, Alan R. Liss, Inc., Publisher, New York, N.Y., USA, 1987.
Fulton, R. W., Hessmand, B, Johnson, B. J. et al. "Evaluation of diagnostic test used for detection of bovine viral diarrhea virus and prevalence of subtypes 1a, 1b and 2a in persistently infected cattle entering a feedlot," *J. Am. Vet. Med. Assoc.*, 228(4):578-584, 2006.
Gillespie, J. H., J. A. Baker, and K. McEntee, "A cytopathogenic strain of virus diarrhea virus," *Cornell Vet.*, 50:73-79, 1960.
Hofmann, M. A., Brechtbuhl, K., and Stauber, N., "Rapid characterization of new *pestivirus* strains by direct sequencing of PCR-amplified cDNA from the 5' non-coding region," *Arch. Virol.*, 139:217-229, 1994.
Holland et al., *Proc. Natl. Acad. Sci. USA*, 88:7276-7280, 1991.
Liess, B., H. R. Frey, H. Kittsteiner, F. Baumann, and W. Neumann, "Bovine mucosal disease, an immunobiological explainable late stage of BVD-MD virus infection with criteria of a 'slow virus infection,'" *Dtsch. Tieraerzti. Wschr.*, 81(2):481-487, 1974.

Malmquist, W. A., "Bovine viral diarrhea mucosal disease: etiology, pathogenesis, and applied immunity," *J. Am. Vet. Med. Assoc.*, 152:763-768, 1968.

McNulty M. S., Allan G. M., "Application of immunofluorescence in veterinary viral diagnosis," In: Recent advances in virus diagnosis, McNulty M S, McFerran JB (Eds.), pp. 15-26. Martinus Nijhoff, The Hague, Netherlands, 1984.

Olafson, P., A. D., MacCallum, and F. H. Fox, "An apparently new transmissible disease of cattle," *Cornell Vet.*, 36:205-213, 1946.

Ozaki et al., *Nucl. Acids Res.*, 20:5205-5214, 1992.

Paton, D. J., "*Pestivirus* diversity," *J. Comp. Pathol.*, 112(3): 215-236, 1995.

Pellerin, C., J. van den Hurk, J. Lecomte, and P. Tussen, "Identification of a new group of bovine viral diarrhea virus strains associated with severe outbreaks and high mortalities," *Virology*, 203(2):260-268, 1994.

Ramsey, F. K., and W. H. Chivers, "Mucosal disease of cattle," *North Am. Vet.*, 34:629-633, 1953.

Ranheim, T, Mathis, P. K., Joelsson, D. B. et al., "Development and application of a quantitative RT-PCR potency assay for a pentavalent rotavirus vaccine (Rota Teq®)," *J. Virol. Meth.*, 131:193-201, 2006.

Ridpath, J. F., and Bolin, S. R., "Differentiation of types 1a, 1b, and 2 bovine virus diarrhea virus by PCR," *Molec. Cell. Probes*, 12:101-106, 1998.

Ridpath, J. F., S. R. Bolin, and E. J. Dubovi, "Segregation of bovine viral diarrhea virus into genotypes," *Virology*, 205 (1):66-74, 1994.

Ridpath, J. F., Bolin, S. R., and Dubovi, E. J., "Segregation of bovine viral diarrhea virus into genotypes," *Virology*, 205: 66-74, 1994.

Ross, C. E., Dubovi, E. J., and Donis, R. O., "Herd problems of abortions and malformed calves attributed to bovine viral diarrhea," *J. Am. Vet. Med. Assoc.*, 188(6):618-619, 1986.

Sambrook et al., *Molecular cloning: a laboratory manual*, 2nd Edition, Cold Spring Harbor Laboratory, Cold Spring Harbor, N.Y., USA, 1989.

Sambrook and Russell, *Molecular cloning: a laboratory manual*, 3rd Edition, Cold Spring Harbor Laboratory, Cold Spring Harbor, N.Y., USA, 2001.

Schalk, J. A. C., de Vries, C. G. J. C. A., and Jongen, P. M. J. M., "Potency estimation of measles, mumps and rubella trivalent vaccines with quantitative PCR infectivity assay," *Biologicals*, 33(2):71-79, 2005.

Schalk, J. A. C., Elzen, C. V. D., Ovelgonne, H, et al., "Estimation of the number of infectious measles viruses in live virus vaccines using quantitative real-time PCR," *J. Virol. Meth.*, 117:179-187, 2004.

Schefers, J., Munoz-Zanzi, C., Collins, J. E., Goyal, S. M., and Ames, T. R., "Serological evaluation of precolostral serum samples to detect Bovine viral diarrhea virus infections in large commercial dairy herds," *J. Vet. Diagn. Invest.*, 20:625-628, 2008.

Tanner, J. E., and A. P. Morgan, "Design and analysis of veterinary vaccine efficacy trials," *Vet. Microbiol.*, 37(3-4): 221-230, 1993.

Tautz, N., Elbers, K., Stoll, D., Meyers, G., and Thiel, H. J., "Serine protease of pestiviruses: determination of cleavage sites," *J. Virol.*, 71(7):5415-5422, 1997.

Thiel et al., "The *pestiviruses*," In Virology, Fields et al., (eds.) (Lippincott-Raven, Philadelphia, Pa., USA), pp. 1059-1073, 1996.

Vilcek, S, Paton, D. J., Durkovic, B, et al. "Bovine viral diarrhea virus genotype 1 can be separated into at least eleven genetic groups." *Arch. Virol.*, 146:99-115, 2001.

Wang, F, Puddy, A. C., Mathis, B. C., et al., "Using QPCR to assign infectious potencies to adenovirus based vaccines and vectors for gene therapy: toward a universal method for the facile quantitation of virus and vector potency," *Vaccine*, 23:4500-4508, 2005.

Wiskerchen, M., and M. S. Collett, "*Pestivirus* gene expression: protein p80 of bovine viral diarrhea virus is a proteinase involved in polyprotein processing," *Virology*, 184(1): 341-350, 1991.

Wren, G., "New Thinking on BRSV: Research into BRSV and vaccines reveals new information about how the virus behaves and how it may interact with killed vaccines," *Bovine Veterinarian*, (February) pp. 16-19, 2001.

Xu, J., E. Mendez, P. R. Caron, C. Lin, M. A. Murcko, M. S. Collett, and C. M. Rice, "Bovine viral diarrhea virus NS3 serine proteinase: polyprotein cleavage sites, cofactor requirements, and molecular model of an enzyme essential for *pestivirus* replication," *J. Virol.*, 71(7):5312-5322, 1997.

Xue, W., D. Mattick, L. Smith, J. Umbaugh, and E. Trigo, "Vaccination with a modified-live bovine viral diarrhea virus (BVDV) type 1a vaccine completely protected calves against challenge with BVDV type 1b strains,", *Vaccine*, 29(1):70-76, Dec. 10, 2010, [epub ahead of print Oct. 27, 2010].

All of the compositions and methods disclosed and claimed herein can be made and executed without undue experimentation in light of the present disclosure. While the compositions and methods of this invention have been described in terms of exemplary embodiments, it will be apparent to those of ordinary skill in the art that variations may be applied to the composition, methods and in the sequence of steps of the methods described herein without departing from the concept, spirit and scope of the invention. More specifically, it will be apparent that certain agents that are both chemically- and physiologically-related may be substituted for the agents described herein while the same or similar results would be achieved. All such similar substitutes and modifications apparent to those of ordinary skill in the art are deemed to be within the spirit, scope and concept of the invention as defined by the appended claims. Accordingly, the exclusive rights sought to be patented are as described in the claims below.

What is claimed is:

1. A method for detecting the presence of a BVDV-1b live virus, the method comprising:
   diluting a sample in (i) an assay plate containing cultured bovine cells in which live virus particles are capable of replicating and (ii) a corresponding reference plate without cells;
   contacting nucleic acids from at least one sample dilution with a BVDV-1b virus-specific primer/probe set, said virus-specific primer/probe set comprising a forward BVDV-1b virus-specific oligonucleotide amplification primer, a reverse BVDV-1b virus-specific oligonucleotide amplification primer, and a BVDV-1b virus-specific oligonucleotide detection probe; and
   performing at least one cycling step, wherein the at least one cycling step is performed using quantitative real-time polymerase chain reaction (qPCR);
   wherein said BVDV-1b virus-specific primer/probe set is useful in detecting the presence of a BVDV-1b viral-specific polynucleotide in a population of polynucleotides obtained from a plurality of bovine virus particles;
   wherein said plurality of bovine virus particles comprises at least one BVDV Type 1b virus particle; and
   wherein a higher level of a signal from a virus-specific oligonucleotide detection probe in the presence of nucleic acids from the assay plate compared to a signal from the virus-specific oligonucleotide detection probe in the presence of nucleic acids from the reference plate indicates the presence of a live bovine virus in the sample.

2. The method in accordance with claim 1, wherein the sample comprises modified, live bovine virus particles contained within a mammalian vaccine.

3. The method in accordance with claim 2, wherein the mammalian vaccine is a Bovine Respiratory Disease Complex (BRDC) or shipping fever vaccine.

4. The method in accordance with claim 1, wherein said plurality of bovine virus particles comprises a plurality of modified, live bovine virus particles; and wherein the plurality of bovine virus particles comprises at least one modified, live BVDV Type 1b virus particle.

5. The method in accordance with claim 4, wherein the plurality of modified, live bovine virus particles further comprises at least one modified, live bovine virus particle selected from the group of a BVDV-1a, BVDV-2, BHV-1, $PI_3$, or an BRSV virus particle.

6. The method in accordance with claim 4, wherein the plurality of modified, live bovine virus particles further comprises at least two different modified, live bovine virus particles selected from the group of a BVDV-1a, BVDV-2, BHV-1, $PI_3$, or an BRSV virus particle.

7. The method according to claim 1, wherein the BVDV-1b virus-specific primer/probe set comprises:
   a forward virus-specific oligonucleotide amplification primer of less than, or about, 50 nucleotides in length comprising a nucleotide sequence of SEQ ID NO: 1;
   a reverse virus-specific oligonucleotide amplification primer of less than, or about, 50 nucleotides in length comprising a nucleotide sequence of SEQ ID NO: 2; and
   a virus-specific oligonucleotide detection probe of less than, or about, 50 nucleotides in length comprising a nucleotide sequence of SEQ ID NO: 3.

8. The method according to claim 1, wherein the at least one virus-specific primer/probe set consists of the nucleotide sequences of SEQ ID NO: 1, SEQ ID NO: 2, and SEQ ID NO: 3.

9. The method in accordance with claim 1, wherein the plurality of bovine virus particles further comprises at least one bovine virus particle selected from the group of a BVDV-1a, BVDV-2, BHV-1, $PI_3$, or BRSV virus particle.

10. The method in accordance with claim 9, wherein the plurality of bovine virus particles further comprises at least two different bovine virus particles selected from the group of a BVDV-1a, BVDV-2, BHV-1, $PI_3$, or an BRSV virus particle.

* * * * *

UNITED STATES PATENT AND TRADEMARK OFFICE
CERTIFICATE OF CORRECTION

| | | |
|---|---|---|
| PATENT NO. | : 9,238,843 B2 | Page 1 of 1 |
| APPLICATION NO. | : 13/995707 | |
| DATED | : January 19, 2016 | |
| INVENTOR(S) | : James Robert Harris and Dale Wade Weise | |

It is certified that error appears in the above-identified patent and that said Letters Patent is hereby corrected as shown below:

Claims

At Column 44, Line 14, In Claim 4, delete "1 b" and insert -- 1b --, therefor.

At Column 44, Line 33, In Claim 7, delete "NO: 2 ;" and insert -- NO: 2; --, therefor.

Signed and Sealed this
Twelfth Day of April, 2016

Michelle K. Lee
*Director of the United States Patent and Trademark Office*

SEQUENCE LISTING

```
<160> NUMBER OF SEQ ID NOS: 21

<210> SEQ ID NO 1
<211> LENGTH: 25
<212> TYPE: DNA
<213> ORGANISM: Artificial Sequence
```

```
-continued

<220> FEATURE:
<223> OTHER INFORMATION: synthetic construct - primer

<400> SEQUENCE: 1
caccctatca ggctgtattc atagc                                           25

<210> SEQ ID NO 2
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 2
tgcccacagc acatcttaac c                                               21

<210> SEQ ID NO 3
<211> LENGTH: 15
<212> TYPE: DNA
<213> ORGANISM: Artificial Sequence
<220> FEATURE:
<223> OTHER INFORMATION: synthetic construct - primer

<400> SEQUENCE: 3
tcacctggac gaccc                                                      15

<210> SEQ ID NO 4
<211> LENGTH: 25
<212> TYPE: DNA
<213> ORGANISM: Artificial Sequence
<220> FEATURE:
<223> OTHER INFORMATION: synthetic construct - primer

<400> SEQUENCE: 4
gcaatgctgc aggactaggt ataat                                           25

<210> SEQ ID NO 5
<211> LENGTH: 25
<212> TYPE: DNA
<213> ORGANISM: Artificial Sequence
<220> FEATURE:
<223> OTHER INFORMATION: synthetic construct - primer

<400> SEQUENCE: 5
acactgtaat tgatgacccc attct                                           25

<210> SEQ ID NO 6
<211> LENGTH: 22
<212> TYPE: DNA
<213> ORGANISM: Artificial Sequence
<220> FEATURE:
<223> OTHER INFORMATION: synthetic construct - primer

<400> SEQUENCE: 6
aagacttgta tgatgctgcc aa                                              22

<210> SEQ ID NO 7
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 7
ggtcgcccag gtaaaagca                                                  19
```

<210> SEQ ID NO 8
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 8
gcctctgcag caccctatca                                           20

<210> SEQ ID NO 9
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 9
aaccgactgt tacgaatac                                            19

<210> SEQ ID NO 10
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 10
gctagccatg cccttagtag gac                                       23

<210> SEQ ID NO 11
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 11
gacgagtccc ctgtactcag g                                         21

<210> SEQ ID NO 12
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 12
cagtgagtcc attggatgg                                            19

<210> SEQ ID NO 13
<211> LENGTH: 22
<212> TYPE: DNA
<213> ORGANISM: Artificial Sequence
<220> FEATURE:
<223> OTHER INFORMATION: synthetic construct - primer

<400> SEQUENCE: 13
ggagaccaag accaaggaga tg                                        22

<210> SEQ ID NO 14
<211> LENGTH: 19
<212> TYPE: DNA
<213> ORGANISM: Artificial Sequence
<220> FEATURE:
<223> OTHER INFORMATION: synthetic construct - primer

```
<400> SEQUENCE: 14
cgtctgccca tgcataagg                                                    19

<210> SEQ ID NO 15
<211> LENGTH: 17
<212> TYPE: DNA
<213> ORGANISM: Artificial Sequence
<220> FEATURE:
<223> OTHER INFORMATION: synthetic construct - primer

<400> SEQUENCE: 15
acctcggtca tccatag                                                      17

<210> SEQ ID NO 16
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 16
ccatgttagc gctctggaac c                                                 21

<210> SEQ ID NO 17
<211> LENGTH: 22
<212> TYPE: DNA
<213> ORGANISM: Artificial Sequence
<220> FEATURE:
<223> OTHER INFORMATION: synthetic construct - primer

<400> SEQUENCE: 17
cgtctttacg gtcgacgact cc                                                22

<210> SEQ ID NO 18
<211> LENGTH: 15
<212> TYPE: DNA
<213> ORGANISM: Artificial Sequence
<220> FEATURE:
<223> OTHER INFORMATION: synthetic construct - primer

<400> SEQUENCE: 18
acggacgtgc gcgaa                                                        15

<210> SEQ ID NO 19
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 19
gtcgtccagg tgaaaacggt                                                   20

<210> SEQ ID NO 20
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 20
gtcgtccagg tgaaaacggt                                                   20

<210> SEQ ID NO 21
```

```
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 21
gtcgtccagg tgaaaacggt                                              20
```